United States Patent
Md et al.

(10) Patent No.: US 11,318,090 B1
(45) Date of Patent: May 3, 2022

(54) IN SITU GELLING COMPOSITION AS A PH-SELECTIVE AND MUCOADHESIVE SUSTAINED RELEASE DRUG DELIVERY SYSTEM

(71) Applicant: King Abdulaziz University, Jeddah (SA)

(72) Inventors: Shadab Md, Jeddah (SA); Samaa T. Abdullah, Jeddah (SA); Nabil A. Alhakamy, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/464,745

(22) Filed: Sep. 2, 2021

Related U.S. Application Data

(62) Division of application No. 17/175,764, filed on Feb. 15, 2021, now Pat. No. 11,260,025.

(51) Int. Cl.
| | |
|---|---|
| *A61K 9/00* | (2006.01) |
| *A61K 47/42* | (2017.01) |
| *A61K 31/05* | (2006.01) |
| *A61K 47/36* | (2006.01) |
| *A61K 9/06* | (2006.01) |
| *B82Y 5/00* | (2011.01) |

(52) U.S. Cl.
CPC ............ *A61K 9/006* (2013.01); *A61K 9/06* (2013.01); *A61K 31/05* (2013.01); *A61K 47/36* (2013.01); *A61K 47/42* (2013.01); *B82Y 5/00* (2013.01)

(58) Field of Classification Search
CPC .......... A61K 9/00; A61K 9/14; A61K 9/1605; A61K 9/1617; A61K 9/1629; A61K 9/1652; A61K 9/1658; A61K 9/1682
See application file for complete search history.

(56) References Cited

U.S. PATENT DOCUMENTS

| | | | | |
|---|---|---|---|---|
| 2017/0112775 A1* | 4/2017 | Dong | .................. | A61K 9/5192 |
| 2017/0208827 A1* | 7/2017 | Riziq | .................... | A61P 19/00 |

* cited by examiner

*Primary Examiner* — Micah Paul Young
(74) *Attorney, Agent, or Firm* — WC&F IP

(57) ABSTRACT

An in situ gelling composition comprising nanoparticles comprising soy protein and a bioactive agent, and a sodium alginate film, wherein the nanoparticles are encapsulated in the film. The in situ gelling composition maybe incorporated into a solid dosage form or reconstituted with water for oral administration to a subject in need of sustained release of the bioactive agent.

9 Claims, 19 Drawing Sheets

IN SITU GELLING COMPOSITION AS A PH-SELECTIVE AND MUCOADHESIVE SUSTAINED RELEASE DRUG DELIVERY SYSTEM

FIELD OF THE INVENTION

The invention is generally related to in situ gelling compositions for the sustained delivery of bioactive agents such as resveratrol.

BACKGROUND OF THE INVENTION

Resveratrol (Rv) is an antioxidant, anti-inflammatory, and anticancer agent. However, Rv requires multiple oral administrations due to high metabolism and low physiochemical stability. Previous studies have provided formulations such as an Rv loaded silica gel prepared using ethanol. The Rv size in the gel was in the micro range, the encapsulation efficiency was 19%, and the drug release reached 80% or 90% of the drug loading as a fast-acting system in pH 2.0 or 7.4 media, respectively (Qin et al. 2020).

In another study, alginate nanoparticles of curcumin and Rv were prepared as a nanosuspension or freeze-dried powder with ethanol. The resulting nanoparticle sizes were 12 nm or 60 nm for the nanosuspension or freeze-dried powder, respectively. The nanoparticles' full release was 87.6% after 8 hrs at pH 8 (Saralkar and Dash 2017).

Floating sodium alginate (NA) beads were formulated by the delivery of self-emulsifying Rv. Beads were prepared by hot drying or freeze-drying. The study claimed the beads' floating was for 72 hrs on the stomach surface. The Rv was formulated as microparticles which achieved a 97.22% or 84.60% after 8 hrs gastric release for the oven-dried or freeze-dried particles, respectively (Fitriani 2017).

In another study, simple physical mixing of NA and Rv was examined (Wang et al. 2015).

Additionally, a Eudragit-coated zein/pectin nanoparticle was formulated as a suspension using ethanol for Rv colonic delivery. The size of the particles was 100-200 nm. Rv's release in pH 3, 7, or 8 was 100% after 200 mins as a fast-acting system for colonic delivery (Contado et al. 2020).

In another related study, a formulation of alginate-shelled Sp nanoparticle for resveratrol encapsulation with enhanced colloidal and chemical stability was described. This liquid formula was directed for food usage with enhanced Rv stability. The size of the particle reached 204.5 nm. Ethanol was used to develop the co-precipitated complex of Sp and Rv and the alginate nanoparticles' final encountering. This previous study did not examine the release of Rv after oral ingestion but instead focused on the physiochemical stability of the formula encountering Rv (Zhang Lingtuo et al. 2019).

While previous studies provided fast-acting formulations, long-acting sustained release and stable formulations for bioactive agents are needed.

SUMMARY

Described herein is a long-acting sustained-release (SR) drug delivery system, which has a pH-selective release and mucoadhesive behavior at the intestinal-colonic area. The formulations provide enhanced physiochemical storage stability of bioactive agents such as resveratrol.

An aspect of the disclosure provides an in situ gelling composition comprising nanoparticles comprising soy protein and a bioactive agent; and a sodium alginate film, wherein the nanoparticles are encapsulated in the film. In some embodiments, the composition forms a gel phase when said composition comes into contact with an acidic media at a temperature at or above 35° C. In some embodiments, the nanoparticles have an average diameter of 350-450 nm. In some embodiments, the sodium alginate has a molecular weight of 400,000-450,000 daltons.

Another aspect of the disclosure provides a solid dosage form comprising an in situ gelling composition as described herein and a pharmaceutically acceptable carrier. In some embodiments, the solid dosage form is selected from the group consisting of a tablet, dragee, capsule, caplet and gelcap.

Another aspect of the disclosure is a solution comprising an in situ gelling composition as described herein reconstituted in water.

Another aspect of the disclosure provides a method of preparing an in situ gelling composition comprising wet granulating a mixture comprising a bioactive agent and soy protein in a granulation fluid to form granules; mixing the granules with a solution containing sodium alginate to form a suspension; and drying the suspension to form an in situ gelling film. In some embodiments, the granulation fluid and the solution do not contain an organic solvent. In some embodiments, the mixture contains a 5:5 to 5:7 ratio of active agent to soy protein. In some embodiments, the method further comprises incorporating the film into a solid dosage form. In some embodiments, the method further comprises reconstituting the film in water.

Another aspect of the disclosure provides a method for the sustained-delivery of a bioactive agent to a subject in need thereof comprising administering an in situ gelling composition as described herein to the subject. In some embodiments, the composition is administered orally.

DETAILED DESCRIPTION

Figure 1:
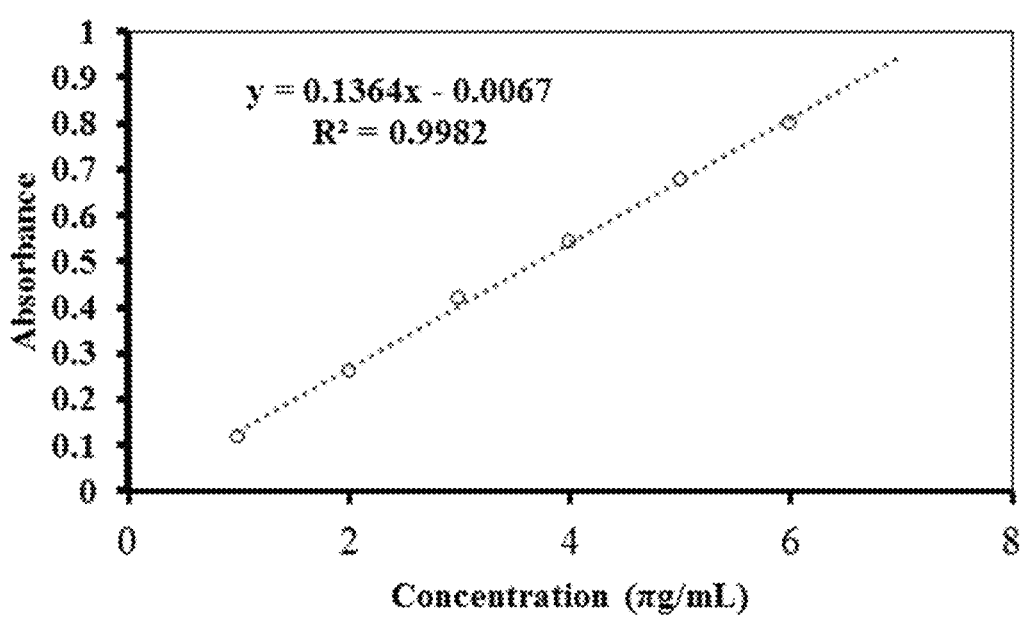
FIG. 1. Rv UV-spectrophotometric calibration curve at 306 nm.

Embodiments of the disclosure provide nanoparticles comprising soy protein and a bioactive agent encapsulated as a nanocomposite in a sodium alginate in-situ gelling film. The film may be administered to a subject after water re-constitution or after incorporation into a solid dosage form, e.g. a gelatin capsule. The formulation provides a long-acting sustained release of the active agent in addition to pH-selective and muco-adherent behavior at the absorption or action site of the intestinal-colonic area. As described in the Example, a film of the disclosure may have a drug encapsulation efficiency of 95% or more, e.g. 96%, 97%, 98%, 99% or more.

Soy protein is a protein that is isolated from soybean. It is made from soybean meal that has been dehulled and defatted. The term "soy protein" encompasses a soy protein isolate which is a highly refined or purified form of soy protein with a minimum protein content of 90% on a moisture-free basis. It is made from defatted soy flour which has had most of the nonprotein components, fats and carbohydrates removed.

Embodiments of the disclosure provide nanoparticles comprising soy protein and an active agent, e.g. a soy protein nanoparticle encapsulating the active agent or soy protein bound/complexed with the active agent. The soy protein enhances the stability of the active agent making it less liable for metabolism. The soy protein may also enhance immune-stimulation for use in cancer management. Additionally, soy protein has a mucosal adhesive property which can increase the active agent cellular uptake, absorption, and localization at the intestinal-colonic area. In some embodiments, In some embodiments, the nanoparticles have an average diameter of about 350-450 nm, e.g. about 380-400 nm.

A "bioactive active agent" refers to an agent capable of eliciting a biological change in a cell (e.g., promoting cell death, apoptosis, decrease in cell proliferative capacity, decrease in mitogenic activity, decrease in migration, inhibiting vascularization, inhibiting angiogenesis and the like). A bioactive agent may be a pharmaceutical agent, drug, compound, or composition that is useful in medical treatment, diagnosis, or prophylaxis. The formulations of the present disclosure are useful for biologically active agents that would benefit from a sustained released upon administration to a human or non-human animal subject. In some embodiments, the active agent is characterized by high metabolism and/or low physiochemical stability. Examples of bioactive agents include, but are not limited to, anticancer agents, antibiotic or antimicrobial (e.g., antibacterial, antifungal, and antiviral) agents, antimetabolic agents, antineoplastic agents, steroids, peptides, proteins, such as, for example, cell receptor proteins, enzymes, hormones, and neurotransmitters, radiolabels such as radioisotopes and radioisotope-labeled compounds, fluorescent compounds, anesthetics, bioactive lipids, polyphenolic active agents, etc. In some embodiments, the active agent is characterized by poor bioavailability. In some embodiments, the active agent is resveratrol. In some embodiments, the film comprises about 0.3-0.7 g resveratrol, e.g. about 0.4-0.6 g or about 0.5 g.

Resveratrol (3,5,4-trihydroxytrans-stilbene) (Rv) is a polyphenolic compound extracted from red grape skin and seeds. It has anti-oxidant, anti-inflammatory, and anticancer activities. Rv has a free radical scavenging activity which provides cancer-protective effects. Rv can activate caspase-3 and caspase-9 and enhance B-cell lymphocyte-associated protein X (BAX) and tumor protein 53 (P53) gene expression to trigger apoptosis of cancerous cells. Rv also triggers the secretion of interferon-gamma (IFN-γ), cytotoxic lymphocytes, T-helper cells, and natural killer cells to capture and limit the growth of cancerous cells. Rv has an inhibitory role in the vascular endothelial growth factor (VEGF) and the release of reactive nitrogen species which are secreted by cancerous cells to enhance the angiogenesis and the creation of the inflammatory environment. Rv's anti-inflammatory properties are due to its negative effects on nuclear factor-kappa beta (NF-kB) and cyclo-oxygenase-1 and -2 (COX-1 and COX-2) (Daemi and Barikani 2012; Isteniĉ et al. 2015; Sergides et al. 2016; Fitriani 2017; Ko et al. 2017; Saralkar and Dash 2017; Salehi et al. 2018; Contado et al. 2020). The high Rv metabolism, especially after oral ingestion, decreases oral bioavailability and increases the need for repetitive administration, associated with Rv adverse effects and diminished patient adherence and compliance (Sergides et al. 2016; Salehi et al. 2018). Additionally, Rv is prone to chemical and physical degradation during storage (Contado et al. 2020).

The nanoparticles described herein are encapsulated in a sodium alginate in situ gelling film. A sodium alginate deposition film has the ability to encapsulate the drug by the conversion of the alginate films into alginic acid gels when in contact with simulated gastric media (e.g. 0.1N—HCl). Alginic acid is a linear copolymer with homopolymeric blocks of (1→4)-linked β-D-mannuronate (M) and α-L-guluronate (G) residues, respectively, covalently linked together in different sequences or blocks. Sodium alginate ($NaC_6H_7O_6$) is the sodium salt of alginic acid. Interactions between sodium alginate and the drug may provide retardant for drug release from soy protein-drug nanoparticles.

In some embodiments, the film comprises about 0.3-0.7 mg/mg sodium alginate, e.g. about 0.4-0.6 mg/mg or about 0.52 mg/mg. In some embodiments, the sodium alginate has a molecular weight of 400,000-450,000 daltons.

In some embodiments, the film comprises about 0.1-0.5 mg/mg soy protein, e.g. about 0.2-0.4 mg/mg or about 0.26 mg/mg.

The films described herein are in situ gelling compositions that provide sustained release of the active agent. There are various changes in conditions that can trigger the gelling of an in situ gelling composition. Among these are changes in pH, osmolality, temperature, water concentration, and alterations in specific ion concentrations.

Temperature-sensitive in situ gelling compositions generally change from a sol to a gel when the temperature exceeds a critical solution temperature, which in the case of drug delivery systems must be reasonably close to body temperature. In some embodiments, the sol-gel transition temperature of the composition of the disclosure is at least 25° C., e.g. at or above about 30° C., e.g. at or above about 35° C., e.g. at or above about 37° C. Alginic acid is a thermosensitive polymer which provides for the gelling of the composition. Other thermosensitive polymers poloxamers, gellan gum, xyloglucan, pectin, chitosan, poly(DL-lactic acid), poly(DL-lactide-co-glycolide) and poly-caprolactone. Suitable solvents for the polymer include water, dimethylsulphoxide, N-methyl pyrrolidone, triacetin and 2-pyrrolidone. In some embodiments, the solvent is not an organic solvent such as ethanol thus avoiding health hazards, the cost of organic solvent removal, and environmental risks associated with organic solvent use.

As used herein, the phrase "sustained release" generally refers to the release of the active agent over an extended period of time leading to relatively lower peak plasma concentrations and a prolonged bioavailability as compared to "immediate release" formulations of the same active ingredient. More precisely, the phrase "sustained release" refers to the release of the drug from the pharmaceutical composition over a period substantially longer than 6 hours, such as about 7, 8, 9, or 10 hours or longer. Generally, the sustained release of drug occurs at such a rate that blood (for example, plasma) concentration in a patient to whom the pharmaceutical composition is administered exhibits reduced levels when compared to blood concentration in a patient to whom an immediate-release formulation is administered. In some embodiments, the film has an entire release of about 10-20% after 8 hours, e.g. about 12-16%, e.g. about 14-15%. The release generally occurs when the film encounters media at a pH of about 6.5 or higher.

Embodiments of the disclosure include solid dosage forms comprising an in situ gelling composition as described herein and a pharmaceutically acceptable carrier. In some embodiments, the solid dosage form is selected from the group consisting of a tablet, dragee, capsule, caplet and gelcap.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. Other suitable excipients include, for example an inert diluent such as lactose; granulating and disintegrating agents such as cornstarch; binding agents such as starch; and lubricating agents such as magnesium stearate.

The disclosure also provides a solution comprising an in situ gelling composition as described herein reconstituted in water. Aqueous suspensions containing the composition may have one or more excipients suitable as suspending agents, for example pharmaceutically acceptable synthetic gums such as hydroxypropyhmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed.

The compositions of the present disclosure may also contain other components such as, but not limited to, antioxidants, additives, adjuvants, buffers, tonicity agents, bioadhesive polymers, and preservatives. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Embodiments of the disclosure include methods of preparing in situ gelling compositions as described herein. The method may comprise wet granulating a mixture comprising a bioactive agent and soy protein in a granulation fluid to form granules; mixing the granules with a solution containing sodium alginate to form a suspension; and drying the suspension to form an in situ gelling film which incorporates the soy protein and bioactive agent as nanocomposites.

In wet granulation, granules are formed by the addition of a granulation fluid onto a powder bed which is under the influence of an impeller (in a high-shear granulator), screws (in a twin screw granulator) or air (in a fluidized bed granulator). The agitation resulting in the system along with the wetting of the components within the formulation results in the aggregation of the primary powder particles to produce wet granules. In some embodiments, the granulation liquid is water. In some embodiments, the granulation fluid does not contain an organic solvent. In some embodiments, the solution does not contain an organic solvent. In some embodiments, the mixture contains a 5:5 to 5:7 ratio of active agent to soy protein. In some embodiments, the method further comprises incorporating the film into a solid dosage form. In some embodiments, the method further comprises reconstituting the film in water.

The present disclosure also provides a method for the sustained-delivery of a bioactive agent to a human or non-human animal subject in need thereof by administering to said subject an in situ gelling composition as described herein.

The compositions of the disclosure may be useful for the treatment of any disease or disorder that the included bioactive agent is useful for treating. For example, if resveratrol is used, the composition or dosage form may be useful for the treatment of ulcerative colitis (inflammatory bowel disease), intestinal-colonic or systemic cancers, osteoarthritis, prostate cancer, gastric cancer, pancreatic cancer, colon cancer, and hepatic cancer. The in situ gelling composition may target the active agent release at the site of action (ulcerative colitis, intestinal and colon cancers) or at the site of absorption to treat systemic cancers (i.e., pancreatic, prostate and hepatic cancers). The compositions are also useful stabilizers for bioactive agent storage.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the active agent (e.g. resveratrol) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject;

the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day. In some embodiments, the composition is administered daily or 2, 3, 4 or more times weekly.

Whilst the beneficial effects of the disclosure are particularly apparent in oral delivery, the utility of the disclosure is not limited and compositions according to the invention may also used for intranasal, buccal, rectal, vaginal, ocular, intraperitoneal, and parenteral drug delivery.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Materials and Methods

Rv Analysis Method Design and Drug-Content Assay

Rv (Sigma-Aldrich, USA) stock solution of 15 µg/mL was prepared in distilled water. Using UV spectrophotometric analysis (Shimadzu-UV-Vis Spectrophotometers, Japan), the analysis was conducted at a wavelength of 306 nm in a 1 cm cell compared to a blank solution of distilled water. To construct a calibration curve, dilutions had been prepared (FIG. 1). The $\lambda$-max selection was based on the UV-scanning from 200-400 nm of pure Rv solution. The formulations' drug-content assays for drug encapsulation efficiency were accomplished by dissolving the formulation in ethanol and centrifuging it for 30 minutes at 1500 rpm. After that, an accurate volume of the supernatant transparent layer had been measured for UV-absorbance at 306 nm for Rv content. This $\lambda$-max was unique for Rv only (Zhang Lingtuo et al. 2019).

Rv-Sp Wet Granulation

The Rv and Sp wet granulation with water was prepared in a 5:6 ratio, respectively, using (ERWEKA FGS II—Wet Granulator, Germany). Using the 5:6 ratio, the Rv daily dose of 500 mg had been encountered in 1.11±0.023 g of the wet granules (Sergides et al. 2016; Ko et al. 2017). The dispersion was left to be dried under the fume-hood. After drying, the wet granules were milled for a particle size of less than 250 µm. The solid dispersion containing 500 mg of Rv was reconstituted with 15 mL distilled water for the drug release experiment. They are represented in Table 1 as Sp 0.6-Rv.

TABLE 1

Composition of formulations of Rv or Rv-Sp solid dispersions (Rv dose is 500 mg)

| Code | NA-level (mg/mg) | Sp-level (mg/mg) | Film (F) or physical mixture (PM) | Rv solid dispersion (SD) or free | Product weight (g) containing 500 mg-Rv* |
|---|---|---|---|---|---|
| NA-Sp-Rv-1200 | 0.52 | 0.26 | F | SD | 2.35 ± 0.013 |
| PM-NA 1200 | 0.52 | 0.26 | PM | Free | 2.31 ± 0.011 |
| Sp 0.6-Rv | — | 0.55 | — | SD | 1.11 ± 0.023 |
| Rv-NA | 0.70 | — | F | Free | 1.71 ± 0.015 |
| Rv | — | — | — | Free | 0.50 ± 0.00 |

*For n = 3± standard deviation.

Nano-Drug Composites on In-Situ Gelling Film Preparation

NA solution of 10% concentration was prepared using a molecular weight grade of 400,000-450,000 g/mole (Sigma-Aldrich, USA). To be homogenized with the Rv:Sp (5:6) granules using a stirrer machine (ERWEKA PRS—Planetary Stirrer, Germany), different volumes of the NA had been optimized to achieve the most optimum SR profile and higher release at the intestinal-colonic simulated media to be recommended for wound healing and anti-inflammatory activities to manage ulcerative colitis of the inflammatory bowel diseases, colorectal cancer or systemic cancers management (Salehi et al. 2018). The Rv-Sp wet granules were homogenized with 0.52 mg/mg of NA containing solution, which was the most optimum amount. After homogenization, the suspension had been transferred and flattened on a glass plate. The film of in-situ gelling ability was formed after over-night drying at room temperature. This film was intended to be given orally as a dry film filled in hard gelatin capsules or reconstituted with 15 mL of water, coded as NA-Sp-Rv-1200.

Drug Release Analysis and Drug Encapsulation Assay

The formulations in Table 1 containing 500 mg of the Rv were each encountered in the dialysis bag (14000 Daltons cut off, Sigma-Aldrich, USA). The dry weights of the formulations were reconstituted with distilled water before enclosing them inside the dialysis bag. The release media volume was 300 mL. The drug-release experiment was designed to simulate the gastrointestinal-pH and transit time after oral ingestion. As a result, the dialysis membranes' surrounding media simulated gastric media (0.1N HCl-pH 1.2), proximal intestine simulated media (phosphate buffer-pH 6.5), the distal area of the small intestine (phosphate buffer-pH 6.8), and phosphate buffer media-pH 7.4 of descending colon simulated media, consecutively. The transit time for each simulated media was two hrs (Amidon et al. 2015; Maurer et al. 2015; Bani-Jaber and Abdullah 2020). The dialysis membranes were subjected to 37±0.5° C. in a water bath shaker of 75 rpm speed. Total release media replacement was made after each hour of dissolution to simulate body sink conditions. This experiment was conducted to optimize the formulation depending on SR behavior and drug encapsulation efficiency. The optimum formula was subjected to aging, gel swelling studies, nanoparticle, and formulation's physiochemical characterizations.

Storage Time Effect on the Nanocomposites of In-Situ Gelling Film

The optimum formula (NA-Sp-Rv-1200) was kept for storage under room temperature. It was stored in an amber glass bottle associated with a desiccant bag to decrease the film's water uptake during storage. The drug release experiments for the formula after 2-, 4- and 8-weeks storage were conducted.

Swelling Study of Nanocomposites of In-Situ Gelling Films-Rv Nanoparticle

The disc-shaped optimum formula was weighed and then immersed in 300 mL of swelling media, similar to the drug release experiment's pH-profile. After 2 hrs of various simulated media, the film's gel was removed from the solution and weighed. The swelling ratio was the mean value of triplicate measurements. The swelling ratio was calculated as the following equation, $$Q=(Ms-Md)/Md$$

Hence, Q is the swelling ratio, Ms is the gel mass after immersing inside the media, and Md is the dry film mass (Tang et al. 2007).

Particle Size Distribution and Zeta-Potential Measurements of the In-Situ Gelling Film NA-Sp-Rv-1200 film's average size after 5 folds dilution with distilled water, size distribution, and poly-dispersity index (PDI) were assessed using Zeta-sizer (Malvern Zetasizer Nano ZS, from Malvern Instruments Ltd., UK). The re-constitution of the film with distilled water was immediately before measurements. They were conducted at 25° C. in an insulated chamber using a dynamic light scattering technique and disposable macro-cells. The zeta-potential evaluation was with disposable measurement cells (DTS 1070, Malvern). All of these measures were made as triplicates.

Chemical and Physical Interactions Elucidation

Using the Fourier transform infrared spectrophotometer (FT-IR) (Thermo-Scientific, Nicolet-iS10, USA), solid sample characterization for interactions was conducted. The studied samples were Rv, Sp, NA, Sp 0.6-Rv wet granules, films of NA-Sp-Rv-1200, and its physical mixtures (PM-NA 1200), Sp-NA films (0.33 mg/mg Sp and 0.67 mg/mg NA), and Rv-NA films (0.5 g Rv and 0.7 mg/mg NA). Dry samples were subjected to compression using the instrument pin. The scan for the samples was at a laser frequency of 15798.7 cm-1 of medium resolution.

X-Ray Diffraction of the Wet Granules and In-Situ Gelling Films

The studied samples were Rv, Sp, NA, Sp 0.6-Rv wet granules, NA-Sp-Rv-1200 and PM-NA 1200, Sp-NA films, and Rv-NA films. They were characterized by the degree of crystallization using a high-resolution X-ray diffractometer (Maxima XRD-7000X, Shimadzu, Japan). X-ray diffractometer scanning speed was 5-80°/min.

Dispersion, Morphology, and Distribution of the Wet Granules and In-Situ Gelling Films Scanning electron microscope (SEM) characterization of Rv, Sp, NA, Sp 0.6-Rv wet granules, films of NA-Sp-Rv-1200, and PM-NA 1200 was done using a microscope (FEI Inspect F50, FEI, Tokyo, Japan) and coater (Emitech K550X, Quorum Technology Ltd., Laughton, UK). Then, they were coated under vacuum with silver and platinum on a metal stub.

Results and Discussion

Drug Release Analysis and Drug Encapsulation Assay

Using the pH-profile drug release, the NA amount, Sp amount, and film preparation method were optimized to achieve a minimum release in the stomach simulated medium, and a higher release with SR behavior in the intestinal and colonic media. The SR-system of pH-selective release aimed to decrease the metabolism associated with the free drug, target the release at the site of action (ulcerative colitis, intestinal and colon cancers) or at the site of absorption to treat the systemic cancers (i.e., pancreatic, prostate and hepatic cancers), and decrease the number of daily doses to enhance the convenience associated with the use of Rv as anti-inflammatory or anticancer treatments (Zheng et al. 2007; Daemi and Barikani 2012; Istenič et al. 2015; Wang et al. 2015; Sergides et al. 2016; Fitriani 2017; Ko et al. 2017; Saralkar and Dash 2017; Ivaniuk et al. 2019; Springer and Moco 2019; Zhang Lingtuo et al. 2019; Contado et al. 2020; Qin et al. 2020).

NA had been used as a deposition film for its ability for SR of the drug by the conversion of the alginate films into alginic acid gels in the contact of simulated gastric media (0.1N—HCl) (Bani-Jaber and Abdullah 2020). The NA potential interaction with Rv was a possible retardant for Rv release, as discussed in the chemical characterization section. Additionally, the Sp might strengthen the alginic acid gel when the Rv was free from the wet granules' Sp, as determined in the chemical characterization section (Zheng et al. 2007).

Figure 2:
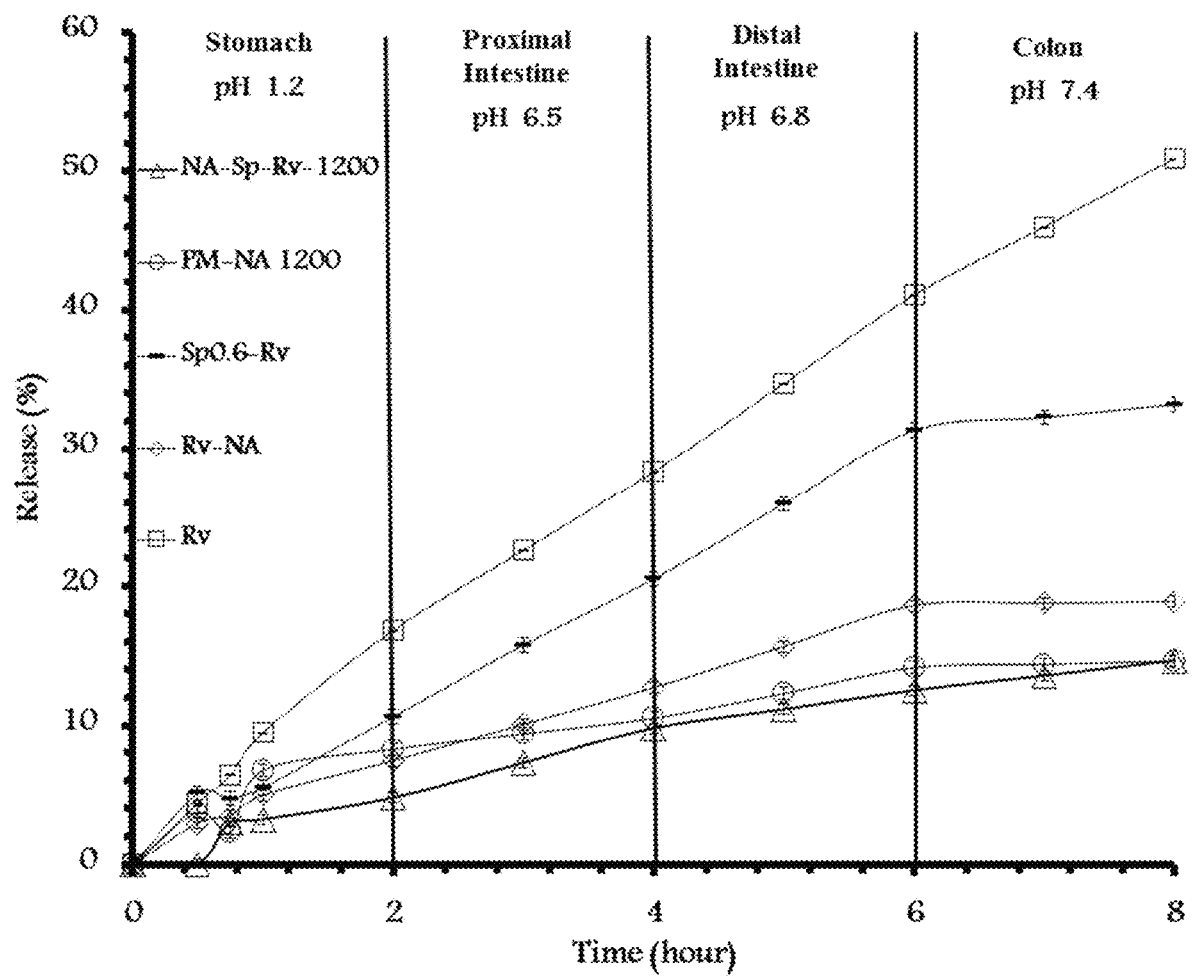
FIG. 2. The pH-profile of the different formulations containing 500 mg of Rv.

The Sp amount was optimized based on its ability to enhance Rv stability (Contado et al. 2020), to be less liable for metabolism (Zhang Lingtuo et al. 2019; Contado et al. 2020), and to enhance immune-stimulation for use in cancer management (Chevreau et al. 1995). Additionally, Sp had been used for its mucosal adhesive property to increase the Rv cellular uptake, absorption, and localization on the intestinal-colonic area after the Sp-Rv wet granules release from the NA gel at pH higher than 6.5 (Zhang Lingtuo et al. 2019; Contado et al. 2020). As in Table 1, a 2.35±0.013 g of film containing 500 mg of Rv was reconstituted with 15 mL distilled water for the drug release experiment. The drug encapsulation efficiency for each formula was done and presented in Table 1. The drug encapsulation efficiency for the optimum formulation NA-Sp-Rv-1200 was 97.87%±0.051. The drug encapsulation efficiency was used to calculate the percentage (%) release of the drug in each formulation. The different formulations were compared for the % gastric release, % intestinal-colonic release, and the entire release as listed in FIG. 2 and Table 2. The studied amounts of Sp were 0.26 and 0.21 mg/mg. The tested amounts of Na were 0.52 and 0.43 mg/mg. The optimum amounts for achieving the intended SR profile, best drug encapsulation, and nanocomposite film formation were 0.52 g and 0.26 mg/mg of NA and Sp, respectively. To study the effect and role of each component, the formulations were examined for their pH-release profile. The Sp effect was essential when comparing the release of Rv with Sp0.6-Rv. The Sp0.6-Rv gastric and intestinal-colonic release was less than the Rv gastric and intestinal-colonic release by 6.21%±0.041 and 11.48%±0.048, respectively. This might be due to the Sp-hydrophobic amino acids surrounding the Rv, which hindered the drug release (Zhang Lifen et al. 2018; Contado et al. 2020).

TABLE 2

Drug release parameters of the different formulations.

| Comparison of Percentage Release | Rv | Sp0.6-Rv | Rv-NA | PM-NA 1200 | NA-Sp-Rv-1200 |
|---|---|---|---|---|---|
| Gastric % Release* | 16.83 ± 0.0041 | 10.62 ± 0.0019 | 7.43 ± 0.0041 | 8.26 ± 0.0013 | 4.59 ± 0.0031 |
| Proximal Intestine % Release* | 11.49 ± 0.0022 | 9.89 ± 0.0018 | 5.27 ± 0.0041 | 2.25 ± 0.0022 | 5.01 ± 0.0036 |
| Distal Intestine % Release* | 12.74 ± 0.0013 | 10.82 ± 0.0031 | 5.89 ± 0.0033 | 3.63 ± 0.0043 | 2.72 ± 0.0021 |
| Colon % Release* | 9.83 ± 0.0044 | 1.87 ± 0.0011 | 0.28 ± 0.0021 | 0.47 ± 0.0019 | 2.13 ± 0.0031 |
| Gastric % Release* | 16.83 ± 0.0041 | 10.62 ± 0.0019 | 7.43 ± 0.0041 | 8.26 ± 0.0013 | 4.59 ± 0.0031 |
| Intestinal-Colonic % Release* | 34.06 ± 0.0051 | 22.58 ± 0.0022 | 11.44 ± 0.0031 | 6.35 ± 0.0022 | 9.86 ± 0.0044 |

*For n = 23± standard deviation

Additionally, the effect of Sp was noticeable when comparing the Rv-NA and NA-Sp-Rv-1200. The NA-Sp-Rv-1200 gastric and intestinal-colonic release was less than the Rv-NA gastric and intestinal-colonic release by 2.66%±0.031 and 1.58%±0.048, respectively. The same Sp's hydrophobic interference might be the reason. Sp's ability to strengthen the NA gel formed in contact with the simulated gastric media, as supported in the FT-IR section, might be an additional explanation (Zheng et al. 2007; Zhang Lingtuo et al. 2019).

To study the NA film's effect, a comparison between NA-Sp-Rv-1200 films and Sp0.6-Rv granules or Rv was made. The NA-Sp-Rv-1200 gastric and intestinal-colonic release was less than the Sp0.6-Rv gastric and intestinal-colonic release by 5.85±0.042 and 12.72%±0.041, respectively. Additionally, the NA-Sp-Rv-1200 gastric and intestinal-colonic release was less than the Rv gastric and intestinal-colonic release by 12.06%±0.012 and 24.2%±0.015, respectively. The minute gastric release of the film and slow rate of the intestinal-colonic release resulted from the formation of the alginic acid gel in contact with 0.1N HCl and the slow dissolution in the pH higher than 4.5, which released the Sp-Rv granules for Sp cellular adherence, uptake or absorption (Zheng et al. 2007; Daemi and Barikani 2012; Istenič et al. 2015; Wang et al. 2015; Fitriani 2017; Saralkar and Dash 2017; Zhang Lingtuo et al. 2019; Bani-Jaber and Abdullah 2020). The alginic acid gel formation with Sp enhancement of the gel strength, Sp hydrophobicity hindrance, and Rv interaction with NA to capture the free Rv were the main reasons for the optimum SR ability of the NA-Sp-Rv-1200 film. NA's significant impact was evident in the release difference between Rv and Sp0.6-Rv versus Rv and NA-Sp-Rv-1200, which was double in the later comparison. This was the final goal of this formulation. The rest of the Rv in the NA-Sp-Rv-1200 (85.55%±0.043) would be released in the colon after 22-71 hours of colon residency, which would be dependent on the food ingestion and disease situation (Amidon et al. 2015; Maurer et al. 2015).

The effect of the unique formulation steps in NA-Sp-Rv-1200 was illustrated compared to the physical mixture of the same constituents (PM-NA 1200). The NA-Sp-Rv-1200 release was less than the gastric release of PM-NA 1200 by 3.49%±0.046, and more than the intestinal-colonic release of PM-NA 1200 by 3.51%±0.034. The time needed for NA to encapsulate the Rv and Sp after wetting with 0.1N HCl might increase the gastric release. On the other hand, the difference in the Sp and Rv's physical mixture gel arrangements, which happened spontaneously depending on the hydrophilic/lipophilic balance, might hinder the Sp hydrophobic amino acids with the Rv inside the NA hydrogel in contact with the intestinal-colonic media. This might lead to lower PM-NA 1200 intestinal-colonic release than the formulated film. Additionally, the surface area of dissolution in the intestinal-colonic area was higher than the physical mixture (Zheng et al. 2007; Zhang Lingtuo et al. 2019).

Storage Time Effect on the Nanocomposites of In-Situ Gelling Film

According to Table 3, the NA-Sp-Rv film was stable during storage for up to 8 weeks, in which the average similarity factor (F2) compared to the freshly prepared film was 95.45%±0.031. This might be a result of the NA and Sp capturing the Rv in a dry film form. This formula is thus an excellent alternative to solve the Rv physical and chemical instability during storage (Contado et al. 2020). F2 was calculated using the following equation.

$$F2 = 50 * \log\left\{\left(1 + \frac{1}{P} * (Rt - Tt)^2\right)^{-0.5} * 100\right\}$$

Where F2 is the similarity factor, and P is the number of release samples. Rt and Tt are dissolution percentages of the compared products. The compared products were dissimilar for drug release performance when the F2 value was less than 50 (Patel et al. 2008).

TABLE 3

Storage time effect on the NA-Sp-Rv-1200 drug release.

| Comparison of Percentage Release | NA-Sp-Rv-1200 | NA-Sp-Rv-1200 (2 weeks) | NA-Sp-Rv-1200 (4 weeks) | NA-Sp-Rv-1200 (8 weeks) |
|---|---|---|---|---|
| Gastric % Release* | 4.59 ± 0.0031 | 4.62 ± 0.0061 | 4.61 ± 0.0025 | 4.63 ± 0.0023 |
| Proximal Intestine % Release* | 5.01 ± 0.0036 | 5.10 ± 0.0037 | 5.09 ± 0.0023 | 5.12 ± 0.0011 |
| Distal Intestine % Release* | 2.72 ± 0.0021 | 2.76 ± 0.0031 | 2.61 ± 0.0051 | 2.63 ± 0.0034 |
| Colon % Release* | 2.13 ± 0.0031 | 2.20 ± 0.0011 | 2.10 ± 0.0031 | 2.03 ± 0.0014 |
| Gastric % Release* | 4.59 ± 0.0031 | 4.62 ± 0.0061 | 4.61 ± 0.0025 | 4.63 ± 0.0023 |
| Intestinal-Colonic% Release* | 9.86 ± 0.0044 | 10.06 ± 0.014 | 9.80 ± 0.0034 | 9.78 ± 0.0044 |

*For n = 3± standard deviation

Swelling Study of Nanocomposites of In-Situ Gelling Films-Rv Nanoparticle

Figure 3:
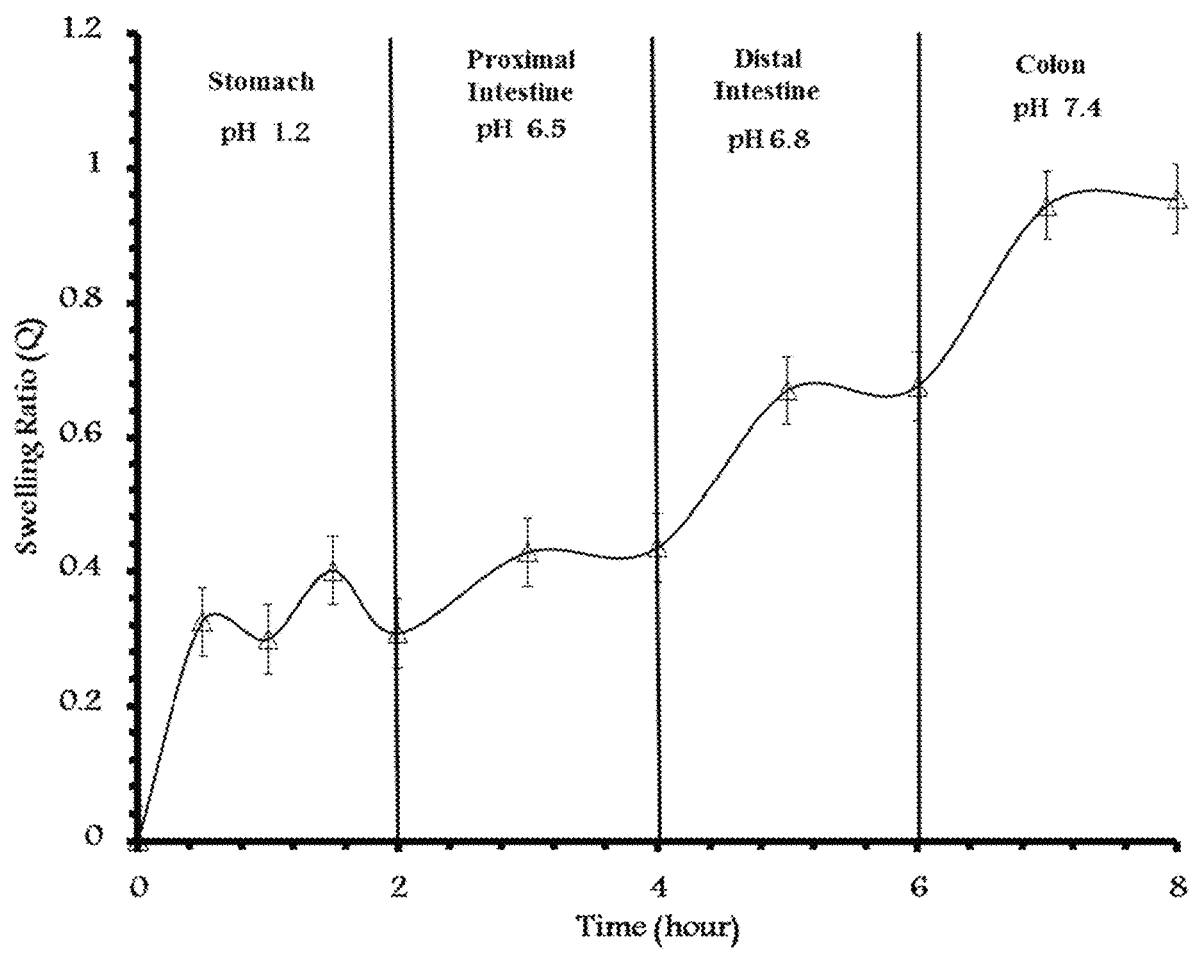
FIG. 3. The pH-effect on the swelling ratio of NA-Sp-Rv-1200.

The swelling of the in-situ gelling optimum formula (FIG. 3) showed an increase in the swelling ratio with the increase in the media's pH from 1.2 up to 7.4. The swelling ratios for NA-Sp-Rv using 1.2 g of NA and 0.6 g of Sp were 0.31±0.031, 0.44±0.041, 0.68±0.011 and 0.95±0.031 at the treatment end of pH 1.2, 6.5, 6.8 and 7.4, respectively. The increase in the swelling ratio came to confirm the drug release increase over the higher values of the pH-profile. As a result, the hydrodynamic gel structure of the Sp-NA in-situ gel was essential for developing the selective pH-SR system. As shown in FIG. 3, fluctuations in the swelling ratio in the simulated gastric phase during 2 hrs might be due to the equilibrium that happened to the NA after alginic acid gel formation. These specific amounts of 0.52 mg/mg NA and 0.26 mg/mg Sp in the optimum formula were characterized with a fewer swelling ratio at the pH 1.2 and 6.5, and higher swelling rates of change with more sensitivity to the pH change at the pH 6.8 (area of Rv absorption) and 7.4 than the formula containing 0.43 mg/mg of NA and 0.21 mg/mg of Sp. The formula of 0.43 mg/mg of NA and 0.21 mg/mg of Sp showed a higher swelling ratio at pH 1.2 and 6.5 than the NA-Sp-Rv-1200 formula. Additionally, it revealed a similar rate of the swelling ratios' change at pH 6.8 and 7.4 to the pH 1.2 and 6.5 of the formula containing 0.6 g of NA and 0.3 g of Sp. The Sp percentage in the formulation tailored and determined the swelling ratio with the NA percentage used (Tang et al. 2007; Zheng et al. 2007; Zhang Lingtuo et al. 2019).

Figure 4A:
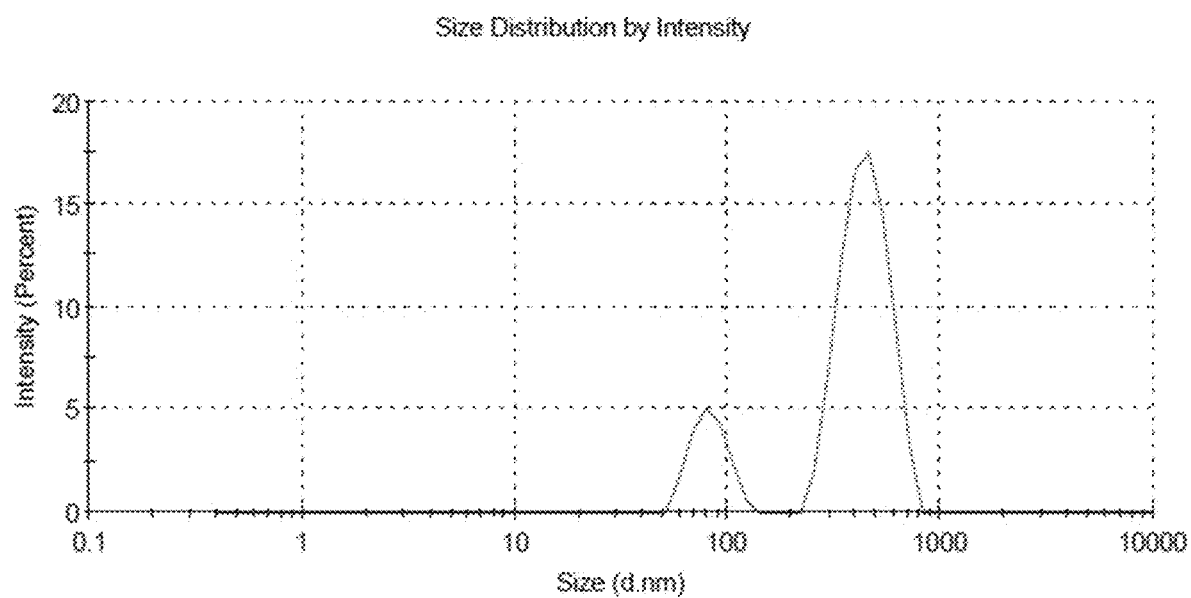
FIGS. 4A-B. The NA-Sp-Rv-1200 particle size distribution (A) and zeta-potential measurement (B).
Figure 4B:
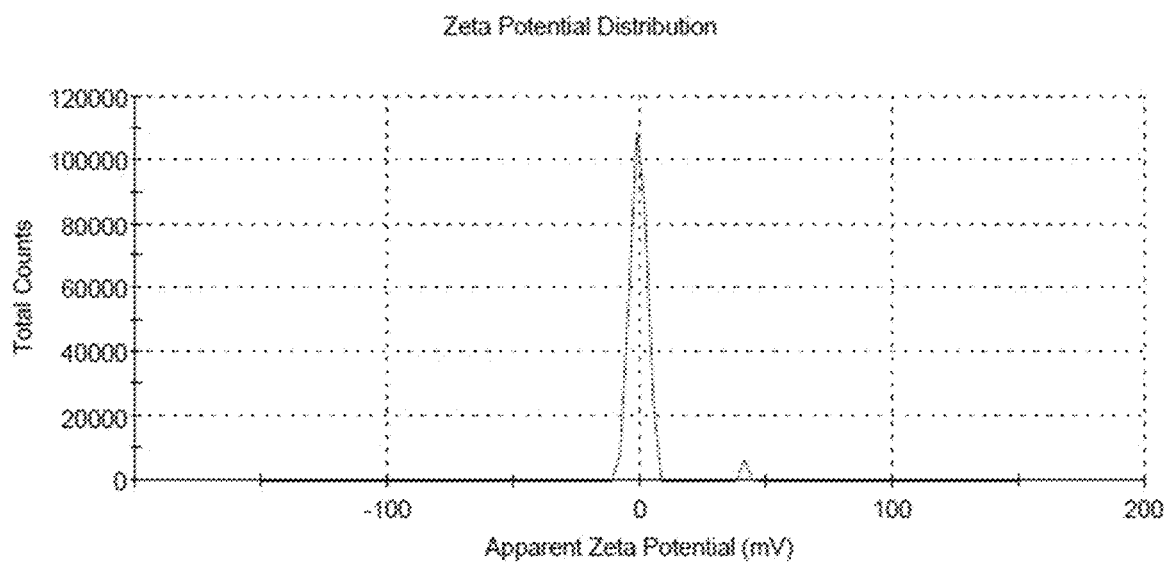

Particle Size Distribution and Zeta-Potential Measurements of the In-Situ Gelling Film The Rv's average particle size in the film was 392.8±0.043 nm, which was considered as a nano-drug composite film containing particles in the range of 1-1000 nm (Md et al. 2020). The confirmation of this result was done by the SEM picture of the NA-Sp-Rv film. The two peaks of particle size populations were 450.5±0.034 nm (82.1%) and 82.66±0.041 nm (17.9%) (FIG. 4A). These results were associated only with this ratio of combined constituents (2:1:0.9 of NA:Sp:Rv, respectively) and the method of preparation resulting from the formula optimization. When the NA amount was increased, the shearing force incidence in the mixing increased, and particle size reduction happened (Istenič et al. 2015; Zhang Lingtuo et al. 2019; Bani-Jaber and Abdullah 2020; Contado et al. 2020). The nanoparticle encapsulation of the drug and Sp inside the NA film would result in the SR behavior results during the drug release experiment, FT-IR, and the powder X-ray diffractions (PXRD) findings. In general, the nanoparticles might have better drug efficacy, sensitivity, lower susceptibility for gastrointestinal metabolism, and longer half-life. This would enhance Rv profile in-vivo (Mourdikoudis et al. 2018; Md et al. 2020). The zeta-potential value of −0.235±0.012 mV (FIG. 4B) might be a result of the NA encapsulation (carboxylate negative charge), which was neutralized in the presence of Sp and Rv (Zheng et al. 2007; Istenič et al. 2015; Mourdikoudis et al. 2018; Zhang Lingtuo et al. 2019). As a result, the electrical conductivity was 4.79±0.12 mS/cm. The PDI was 0.488, which was not used for shelf stability indication because of the solid dosage form used. As a result of the nanoparticles being in the solid-state, the zeta-potential value and PDI value of less than one gave an idea of the particle aggregation tendency in the body after suspending in the gastrointestinal fluids (Mourdikoudis et al. 2018).

Chemical and Physical Interactions Elucidation

Figure 5A:
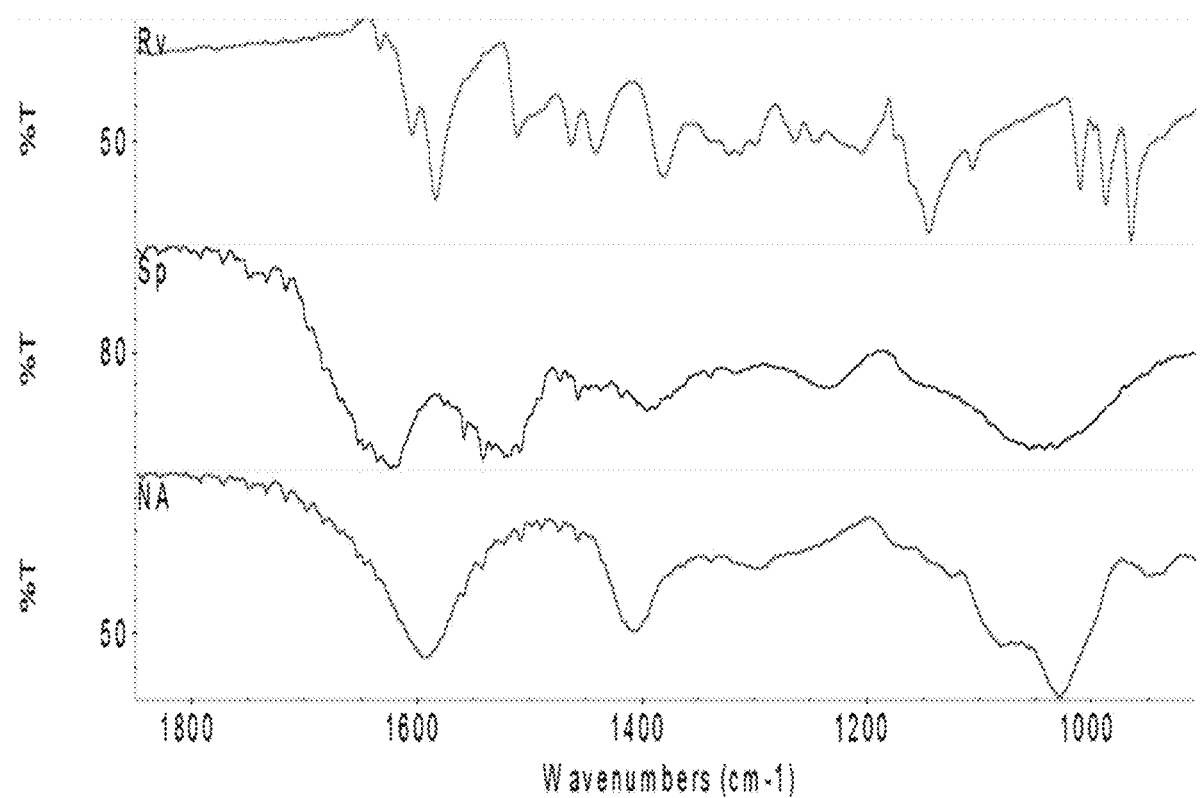
FIGS. 5A-D. The FT-IR spectra of Rv, Sp and NA (A); Sp0.6-Rv, NA-Sp-Rv-1200 and PM-NA 1200 (B); Sp-NA (C); and Rv-NA (D).
Figure 5B:
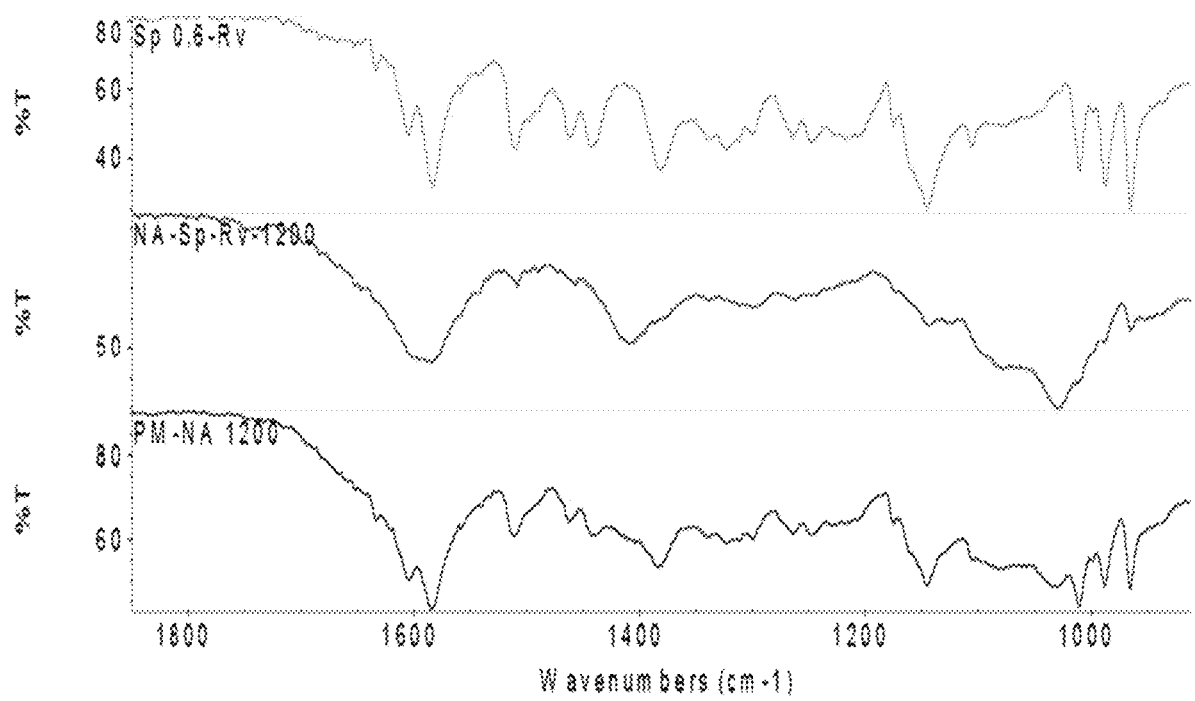
Figure 5C:
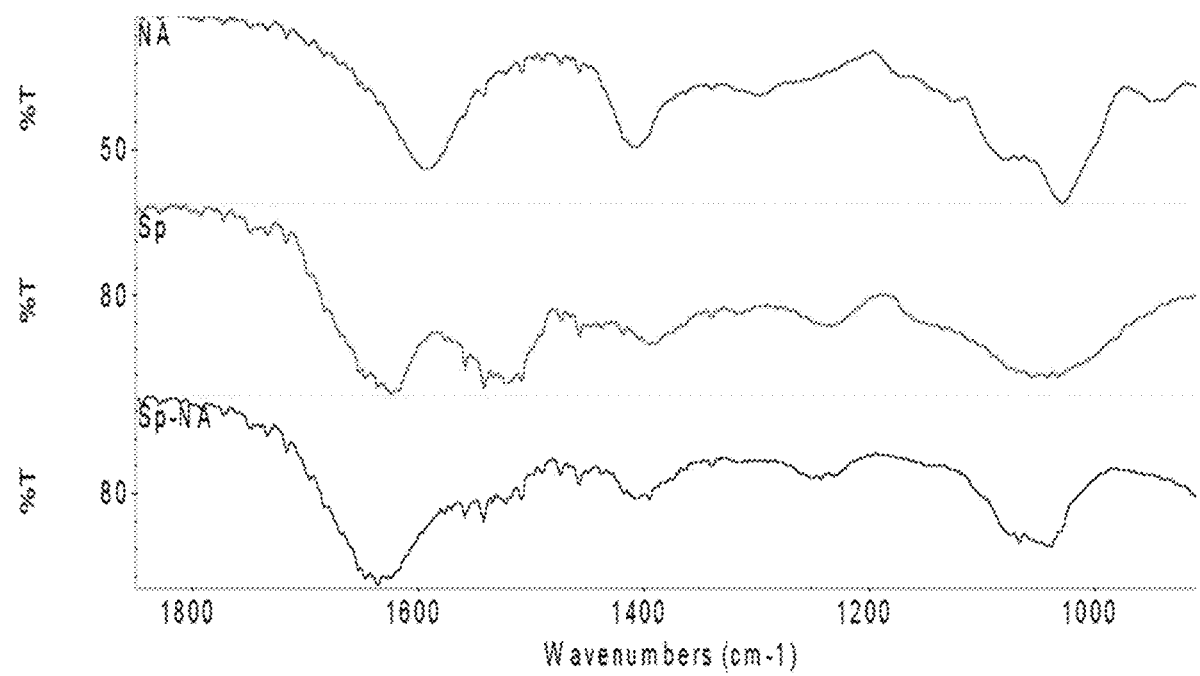
Figure 5D:
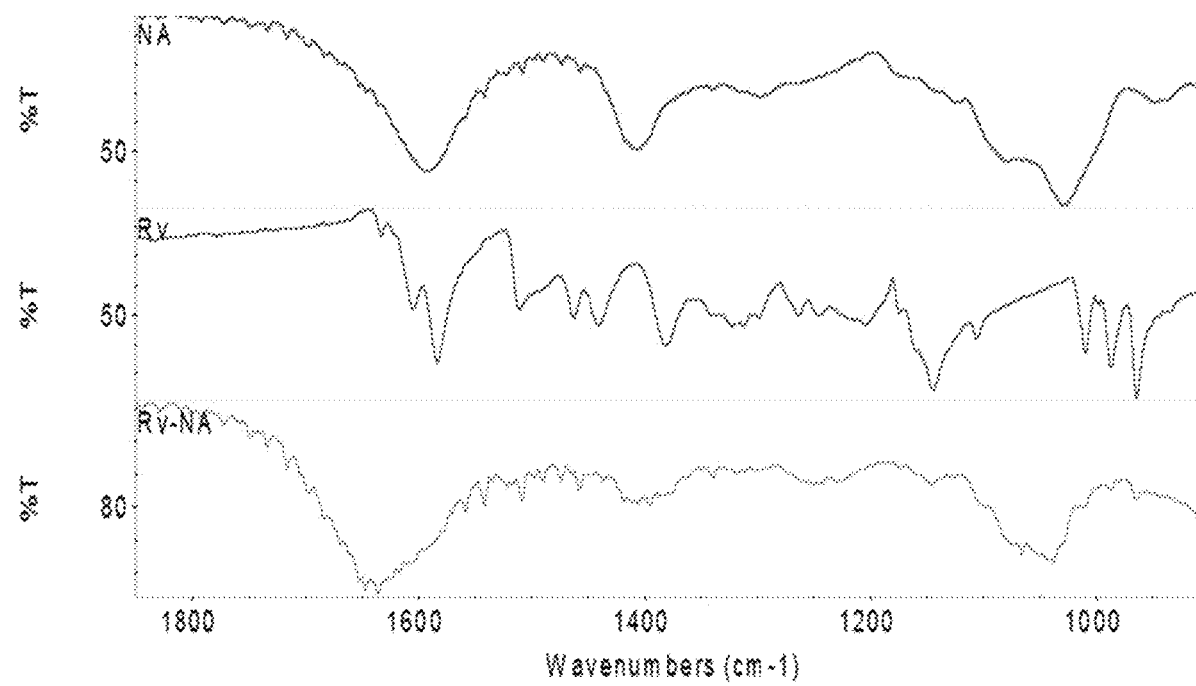
Figure 6A:
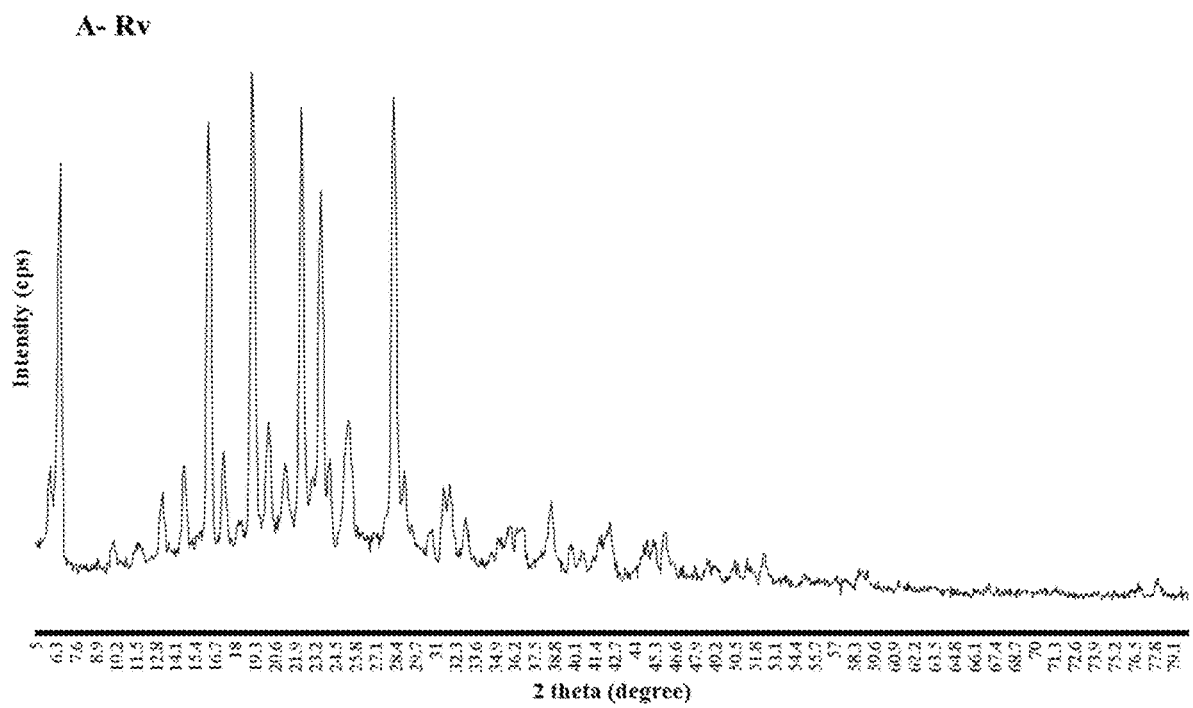
FIGS. 6A-H. The PXRD diffractograms of Rv (A), Sp (B), NA (C), Sp0.6-Rv (D), PM-NA 1200 (E), NA-Sp-Rv-1200 (F), Sp-NA (G), and Rv-NA (H).
Figure 6B:
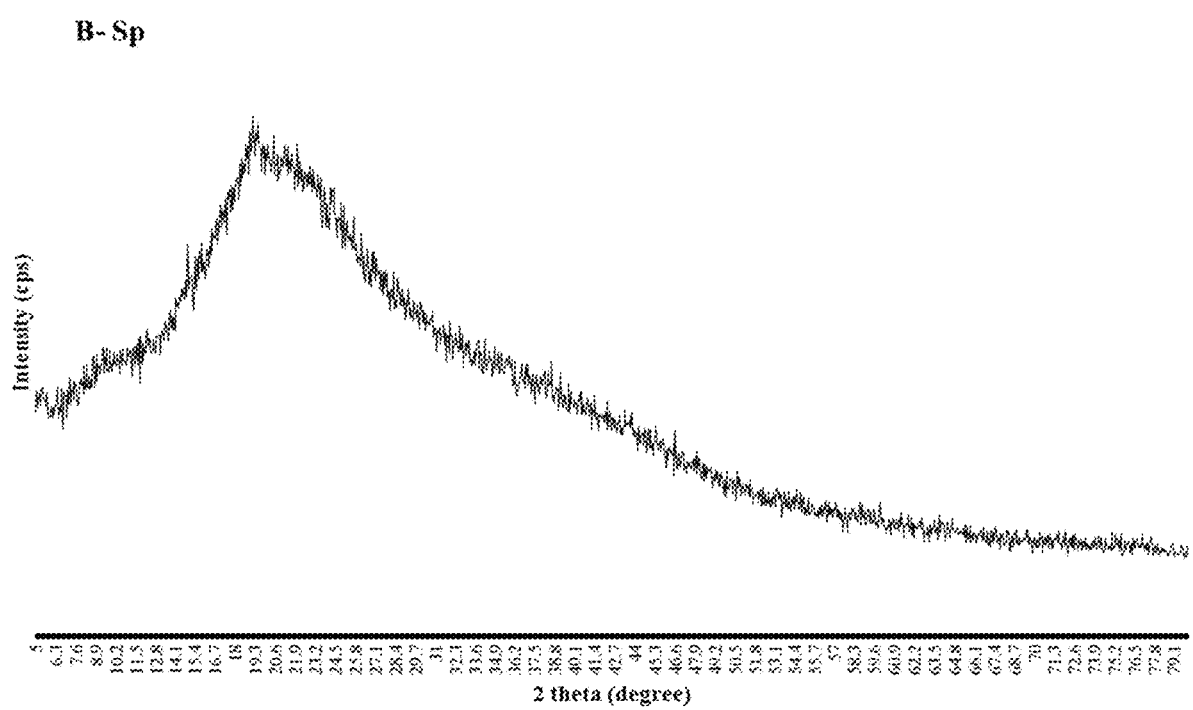
Figure 6C:
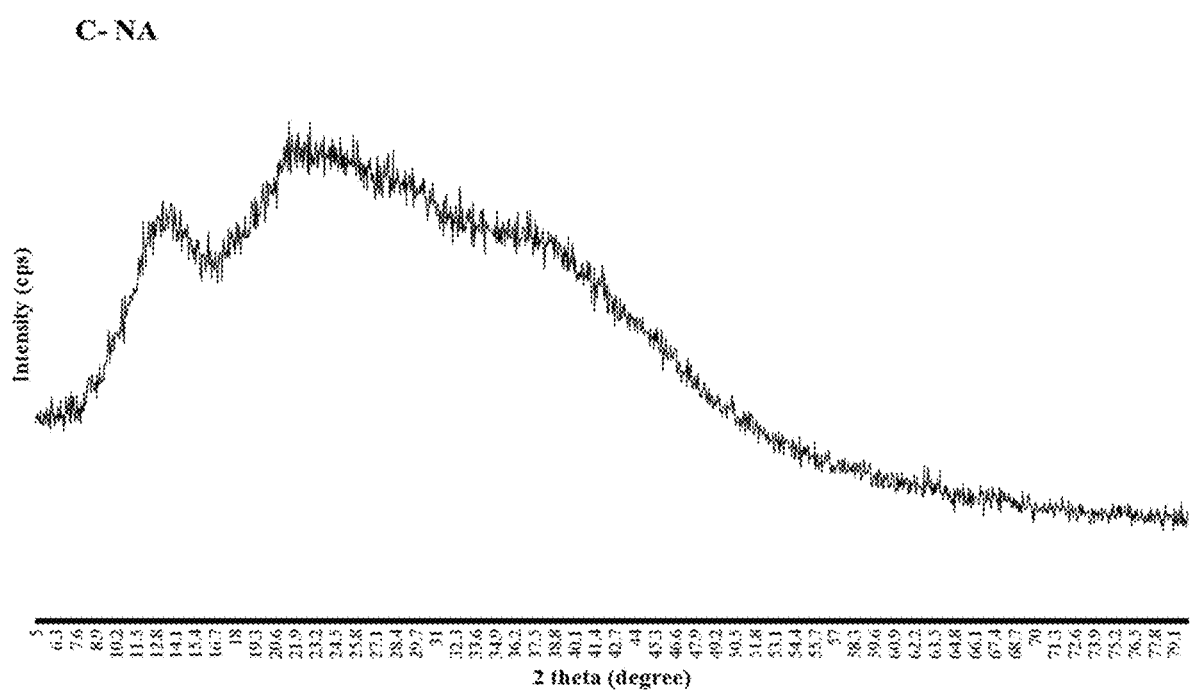
Figure 6D:
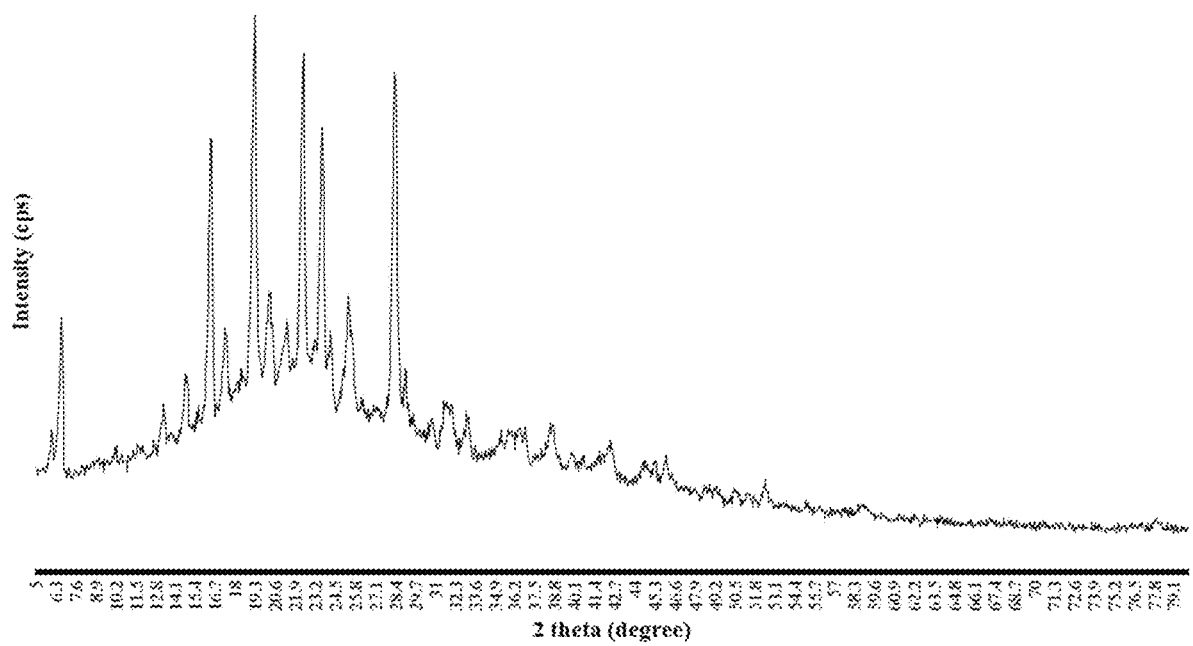
Figure 6E:
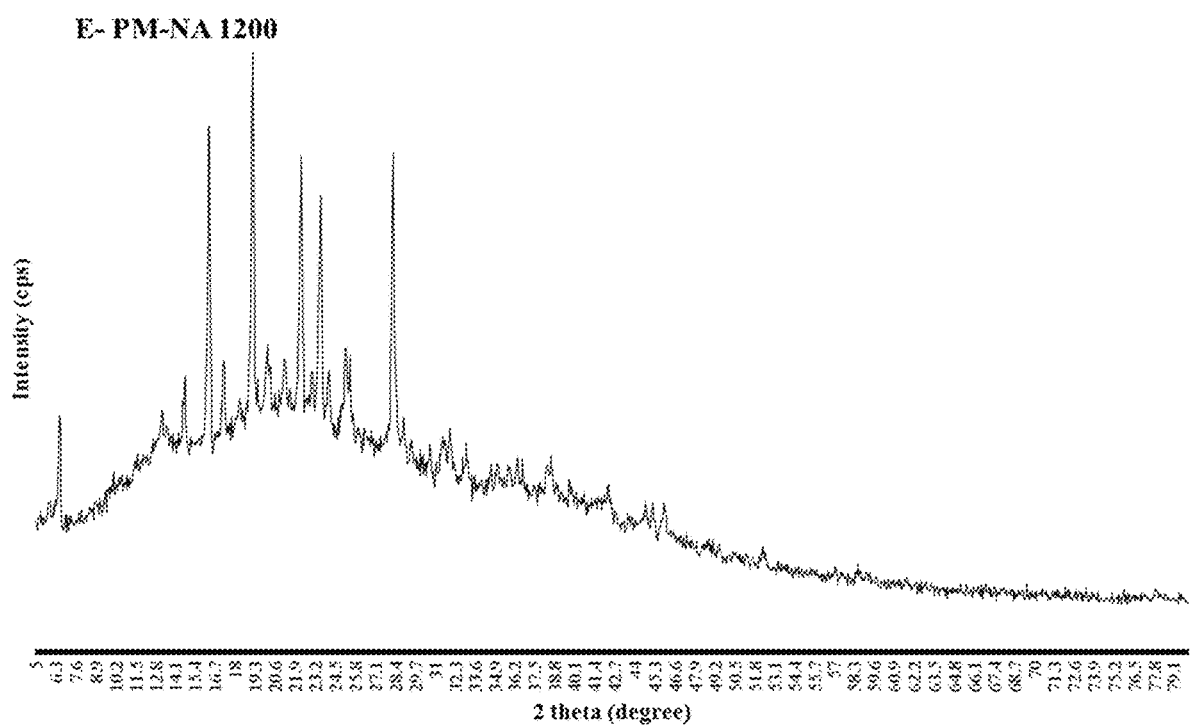
Figure 6F:
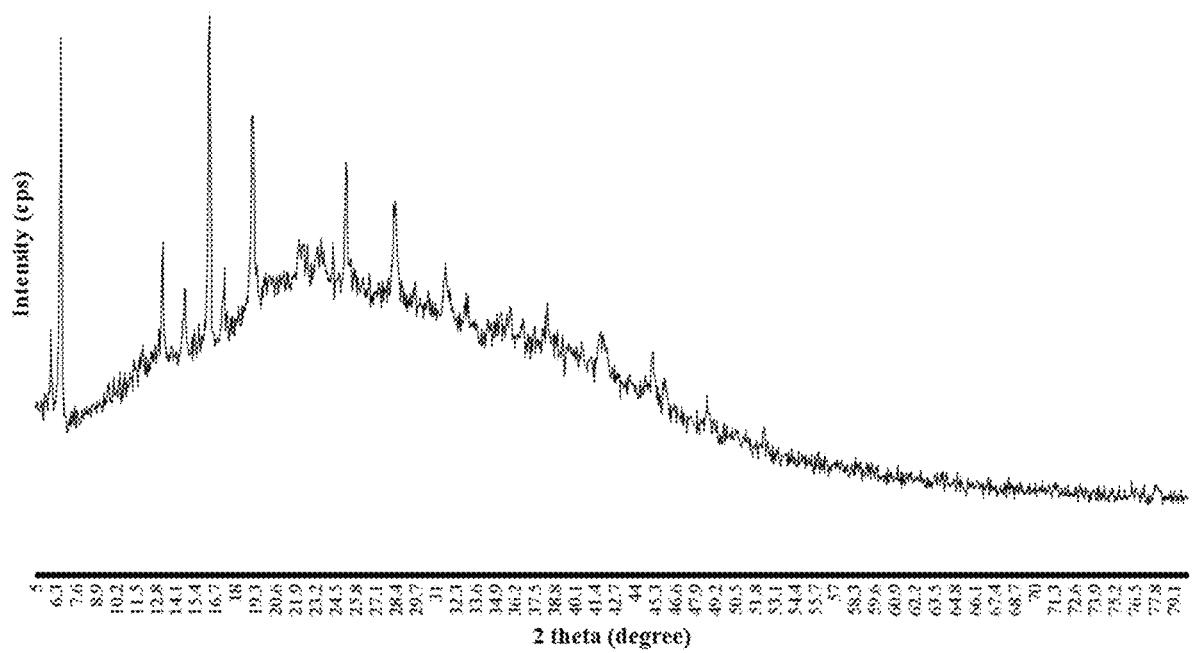
Figure 6G:
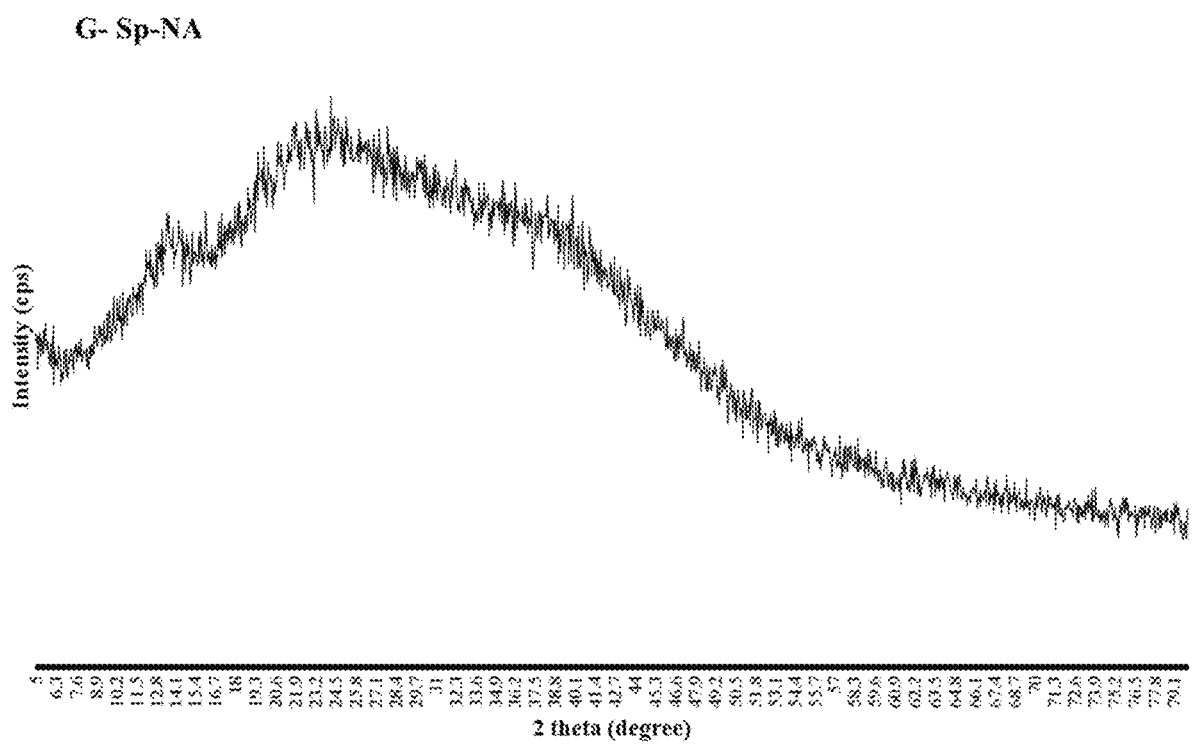
Figure 6H:
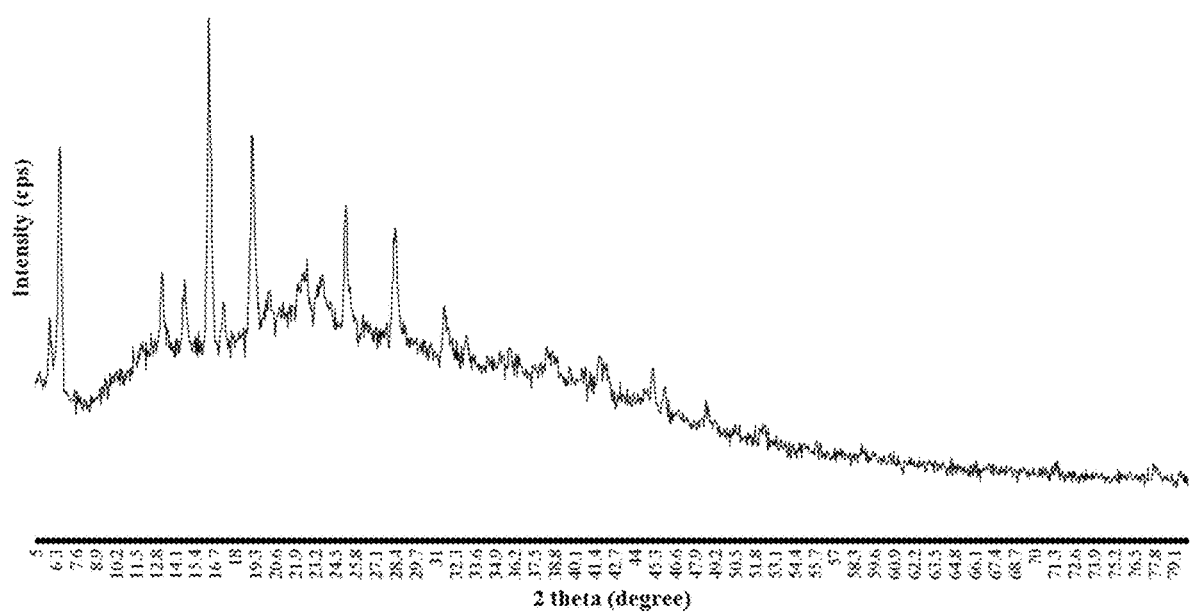
Figure 7A:
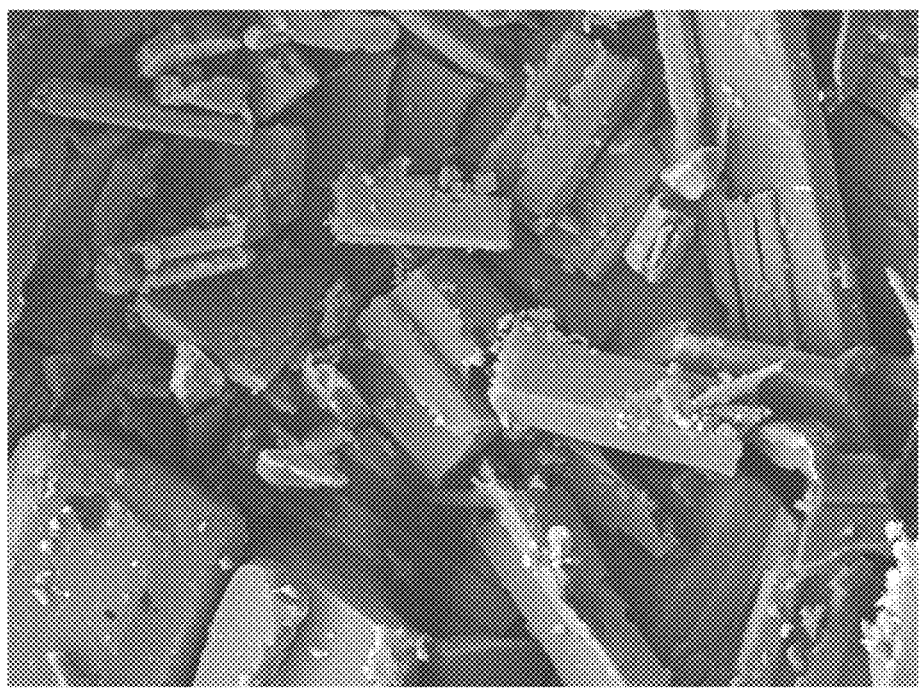
FIGS. 7A-F. The SEM morphological distributions of Rv (A), Sp (B), NA (C), Sp0.6-Rv (D), PM-NA 1200 (E), and NA-Sp-Rv-1200 (F).
Figure 7B:
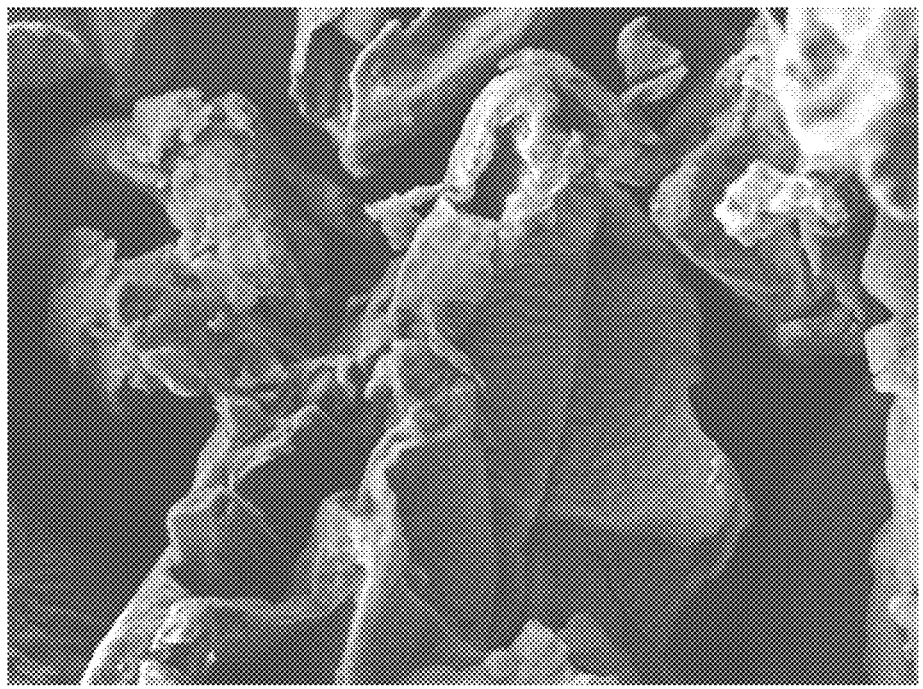
Figure 7C:
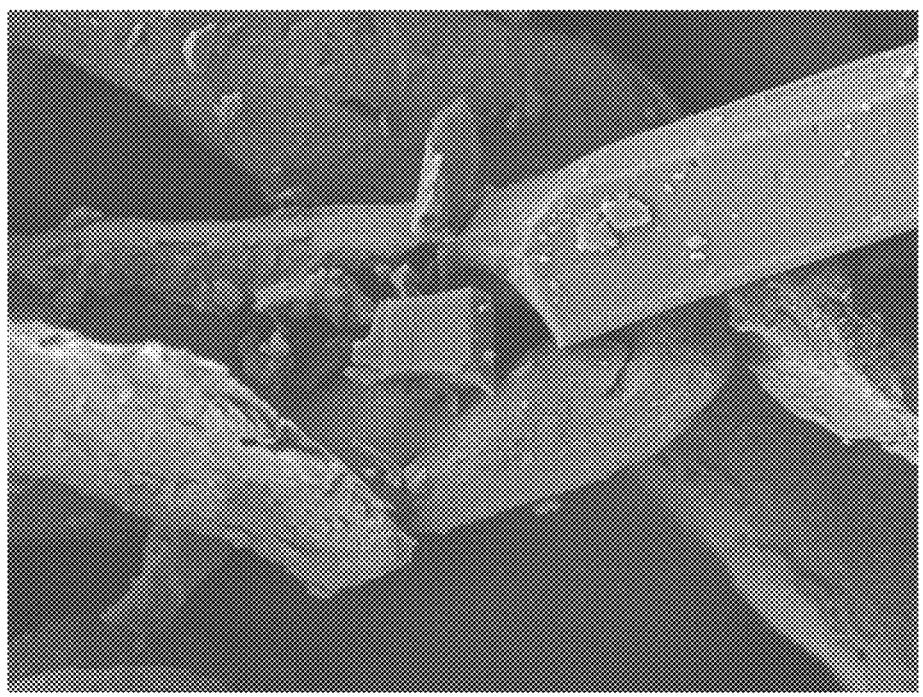
Figure 7D:
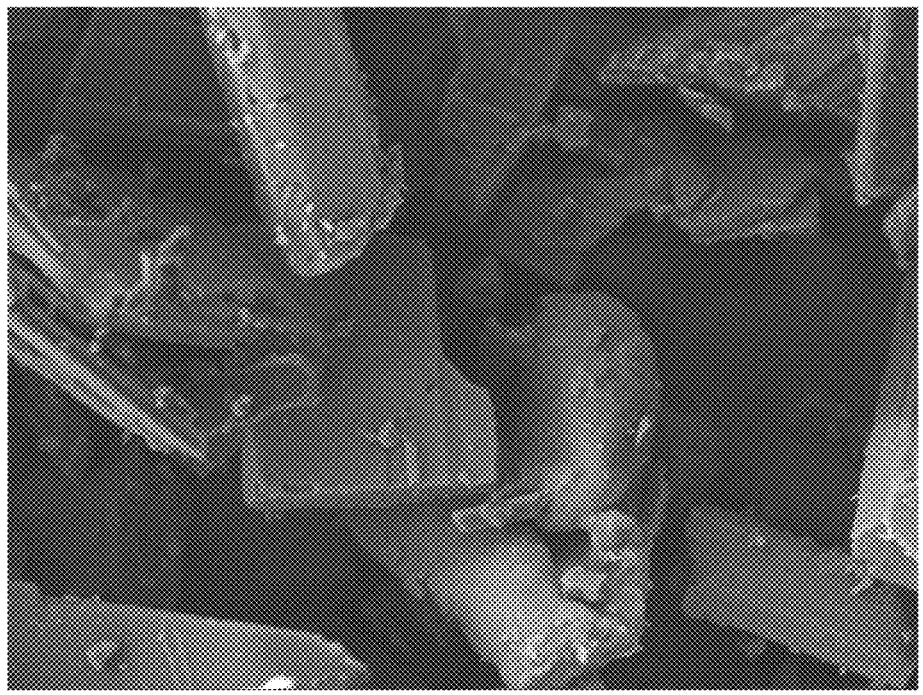
Figure 7E:
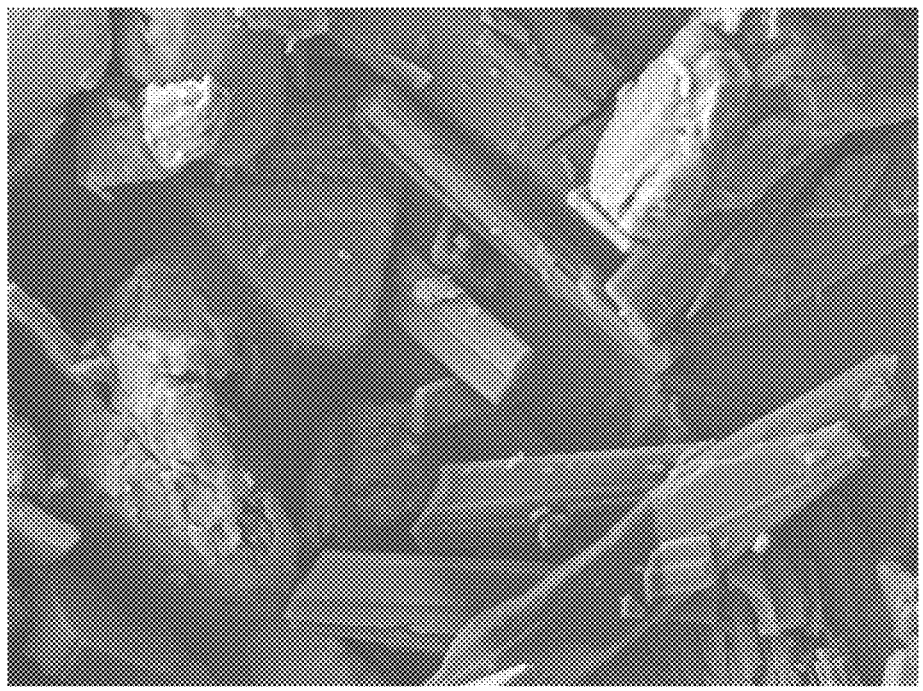
Figure 7F:
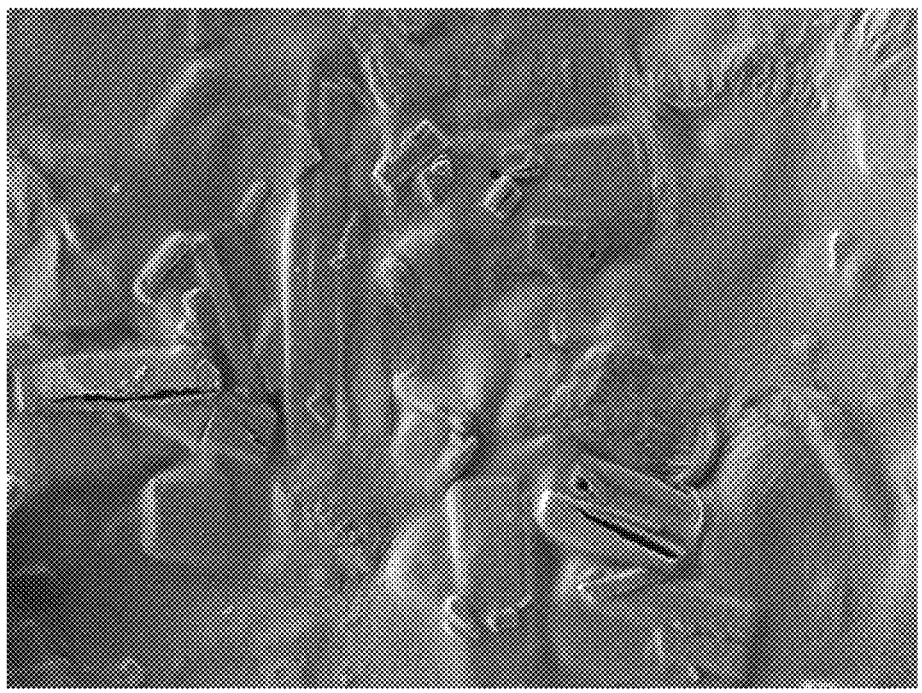

According to FIG. 5 (A-D), FT-IR spectra were elucidated for Rv (FIG. 5A), Sp (FIG. 5A), NA (FIG. 5A), Sp0.6-Rv (FIG. 5B), PM-NA 1200 (FIG. 5B), NA-Sp-Rv (FIG. 5B), Sp-NA (FIG. 5C), and Rv-NA (FIG. 5D). They were analyzed for the potential interactions between the constituents, which affect the drug release, and the other physical characteristics of the optimum nanocomposite film (NA-Sp-Rv). Regarding the Rv spectrum (FIG. 5A), the carbon-carbon aromatic double-bond vibration and carbon-carbon olefinic vibration were at 1606 cm$^{-1}$ and 1587 cm$^{-1}$, respectively. The benzene ring vibrations were revealed at 1513 cm$^{-1}$ and 1463 cm$^{-1}$. The peak of 1384 cm$^{-1}$ was carbon-oxygen vibration. The peak of carbon=carbon-hydrogen and demonstration of the "trans" form of resveratrol were 988 cm$^{-1}$ and 966 cm$^{-1}$ peaks (Istenič et al. 2015). The spectrum of Sp (FIG. 5A) with an amide I peak of the carbon-nitrogen bond was 1626.35 cm$^{-1}$. The amide II band of 2/3 nitrogen-hydrogen stretch and 1/3 carbon-nitrogen bond was approximately at 1521.08 cm$^{-1}$. The amide III band of carbon-nitrogen bend and nitrogen-hydrogen bend was approximately 1400 cm$^{-1}$ (Zheng et al. 2007). NA spectrum (FIG. 5A) revealed essential peaks of hydroxyl, ether, and carboxylic functional groups. At 1595 cm$^{-1}$ peak, it was related to asymmetric stretching vibrations of carboxylate salt ion. This and later peak were essential and used to characterize alginate structure from its derivatives and ingredients. The carbon-oxygen bond peak of pyranose ring, carbon-carbon-hydrogen bond, and carbon-oxygen-hydrogen bond deformations were at 1400 cm$^{-1}$ and 1010 cm$^{-1}$ (Zheng et al. 2007; Daemi and Barikani 2012; Zhang Lingtuo et al. 2019). The spectrum for the physical mixture (FIG. 5B) of NA, Sp, and Rv (PM-NA 1200) revealed a blend of all constituents' peaks. The spectrum of Sp0.6-Rv wet granules (FIG. 5B) showed the Rv peaks with Sp peaks' disappearance. This might result from the Rv disposition on the Sp surfaces or by the Sp dispersion and particle size reduction of Sp between the Rv larger particle (Mourdikoudis et al. 2018). This could be confirmed by the SEM results in the next sections. The in-situ gelling films of the NA-Sp-Rv spectrum (FIG. 5B) represented the NA same essential peaks with 966 cm-1-Rv peak. This would lead to the conclusion of the NA encapsulation or the particle size reduction of Rv and Sp inside the gel, which could be confirmed by the SEM result in the next sections (Mourdikoudis et al. 2018).

For elucidation of the expected molecular interaction and arrangements between NA and Sp in the in-situ gelling film, the Sp-NA film spectrum (FIG. 5C) showed the disappearance of NA-1595 cm$^{-1}$ peak of carboxylate functionality, the absence of NA peaks in the range (1390-1190 cm$^{-1}$), and the presence of the broad NA-1010 cm$^{-1}$ peak of the pyranose ring functionalities with lower intensity. On the other hand, the Sp peaks of 1626 cm$^{-1}$ and Sp peaks in the range of (1390-1190 cm$^{-1}$) were apparent in the Sp-NA spectrum. The Sp peak of 1520 cm$^{-1}$ was absent in the Sp-NA spectrum. The disappearance of the NA-carboxylate functionality peak and the Sp-amide-II peak was an indication of potential interaction (i.e., hydrogen bond) between these functionalities inside the film, which could attribute to the Sp strengthening the ability for the NA (Zheng et al. 2007; Zhang Lingtuo et al. 2019). The rest of the appeared peaks of certain functionalities might be located on the surface of the film. However, the absent ones might be folded inside the film structure (Mourdikoudis et al. 2018).

To elucidate the interaction between Rv and NA after the release from the Sp0.6-Rv wet granules, the Rv-NA film spectrum (FIG. 5D) revealed a new broad peak at 1620 cm$^{-1}$, which might be a result of merging Rv and NA essential peak at this range. The Rv-NA film showed an absence of Rv peaks with NA peaks of the range 1550-1190 cm$^{-1}$ with significantly diminished intensities. This could be attributed to the interaction between the Rv structure and NA-hydroxyl and carboxylate functionalities, incorporating Rv inside the NA film, and the particle size reduction of Rv inside NA gel (Daemi and Barikani 2012; Istenič et al. 2015).

X-Ray Diffraction of the Wet Granules and In-Situ Gelling Films

PXRD of Rv, Sp, NA, Sp0.6-Rv, PM-NA 1200, NA-Sp-Rv-1200, Sp-NA, and Rv-NA were shown in FIG. 6 (A-H). In FIG. 6A, Rv powder showed characteristic patterns, which might indicate Rv powder's crystalline nature. Regarding Sp (FIG. 6B) and NA (FIG. 6C), they did not show specific diffraction peaks, which could be attributed to the amorphous nature. The wet granules of Sp0.6-Rv showed (FIG. 6D) some well-defined peaks with the dominant amorphous nature of Sp. The physical mixture of the previous raw-materials (PM-NA 1200) showed some of the Rv characteristic diffraction peaks with the noisy peaks of the NA and Sp in FIG. 6E. The PXRD of the NA-Sp-Rv-1200 film (FIG. 6F) confirmed an amorphous nature of the particles. The Sp-NA film (FIG. 6G) had more apparent amorphous/un-regular shape property than the Rv-NA film (FIG. 6H). As a result, the Sp and NA nature and interaction might contribute to the NA-Sp-Rv-1200 film amorphicity.

Dispersion, Morphology, and Distribution of the Wet Granules and In-Situ Gelling Films Using SEM, the size-distribution, shape, and dispersion of Rv, Sp, NA, Sp0.6-Rv, PM-NA 1200, and NA-Sp-Rv-1200 films were observed in FIG. 7 (A-F). Rv rectangular crystals were observed to have a particle size larger than 1 μm (FIG. 7A). On the other hand, Sp powder appeared to have a non-uniform shape with a size larger than 1 μm (FIG. 7B). The NA powder was found to be with a non-uniform shape, which was represented in FIG. 7C. In FIG. 7D, the wet granules of Sp0.6-Rv comprised the Sp particles in size less than the Sp raw material (the small particles), which was distributed in between the Rv rectangular particles. The Sp0.6-Rv result came consistent with the FT-IR wet granules result. The physical mixture picture (FIG. 7E) showed the three constituents in their unique shapes. The NA-Sp-Rv confirmed the NA film-encapsulation of the non-uniform Sp large particulates and small Rv crystals-dot like structures (FIG. 7F). Additionally, the Rv and Sp particle size ranges were confirmed to become smaller in the film than the raw materials. All of these results came consistent and supported the FT-IR, PXRD, particle size analysis, zeta-potential, and drug release results.

CONCLUSION

The Rv drawbacks of high metabolism, need for repetitive administrations and physiochemical instability was solved using the optimum in-situ gel nanocomposite film described herein. The drug release experiment, storage time effects, and drug encapsulation efficiency confirmed the NA-Sp-Rv-1200 film's choice. Each of the components' grade, amount, percentage, way of formulation, and final dosage form determined its SR behavior. The NA-Sp-Rv-1200 film was characterized by 14.45%±0.043 after 8 hrs of the average Rv pH-release profile, which left 85.55%±0.43 of the Rv in the formulation to be liberated in the next 22-72 hrs of colon residency time. The average total free Rv pH-profile release was 50.89%±0.033. Additionally, the optimum formulation release was less in the acidic media than the media of pH more than 6.5, which was the opposite of the Rv free drug release. The drug release results were supported and reasoned using the swelling study, particle size analysis, FT-IR, PXRD, and SEM. The average drug encapsulation efficiency of NA-Sp-Rv-1200 was 97.87%±0.051, which might be related to the kneading and formulation preparation method. The storage time effect experiment suggested that the NA-Sp-Rv-1200 would solve the Rv physiochemical stability problems. The particle size analysis experiment stated that the Rv composites' average size in the Sp-NA film was 392.8±0.043 nm and was confirmed by the SEM findings.

REFERENCES

Amidon S, Brown J E, Dave V S. 2015. Colon-Targeted Oral Drug Delivery Systems: Design Trends and Approaches. AAPS PharmSciTech. 16(4):731-741.

Bani-Jaber A, Abdullah S. 2020. Development and characterization of novel ambroxol sustained-release oral suspensions based on drug-polymeric complexation and polymeric raft formation. Pharmaceutical Development and Technology. 25(6):666-675.

Chevreau N, Wang Y, Funk-Archuleta M. 1995. Effect of diets on 5-fluorouracil and cyclophosphamide toxicity. Nutr Cancer. 23(2):205-220.

Contado C, Caselotto L, Mello P, Maietti A, Marvelli L, Marchetti N, Dalpiaz A. 2020. Design and formulation of Eudragit-coated zein/pectin nanoparticles for the colon delivery of resveratrol. European Food Research and Technology.

Daemi H, Barikani M. 2012. Synthesis and characterization of calcium alginate nanoparticles, sodium homopolymannuronate salt and its calcium nanoparticles. Scientia Iranica. 19(6):2023-2028.

Fitriani R. 2017. New cytotoxic diels-alder type adducts from root cultures of Morus alba var. shalun. American Journal of Ethnomedicine. 04(02).

Istenič K, Balanč B D, Djordjević V B, Bele M, Nedović V A, Bugarski B M, Ulrih N P. 2015. Encapsulation of resveratrol into Ca-alginate submicron particles. Journal of Food Engineering. 167:196-203.

Ivaniuk O, Yarnykh T, Kovalevska I. 2019. Determination of the Bioadhesion Indicators of Vaginal Gel with Resveratrol and Hyaluronic Acid. EUREKA: Health Sciences. 2:33-39.

Ko J H, Sethi G, Um J Y, Shanmugam M K, Arfuso F, Kumar A P, Bishayee A, Ahn K S. 2017. The Role of Resveratrol in Cancer Therapy. Int J Mol Sci. 18(12).

Maurer J M, Schellekens R C A, van Rieke H M, Wanke C, Iordanov V, Stellaard F, Wutzke K D, Dijkstra G, van der Zee M, Woerdenbag H J et al. 2015. Gastrointestinal pH and Transit Time Profiling in Healthy Volunteers Using the IntelliCap System Confirms Ileo-Colonic Release of ColoPulse Tablets. PLOS ONE. 10(7):e0129076.

Md S, Alhakamy N A, Aldawsari H M, Husain M, Kotta S, Abdullah S T, A. Fahmy U, Alfaleh M A, Asfour H Z. 2020. Formulation Design, Statistical Optimization, and In Vitro Evaluation of a Naringenin Nanoemulsion to Enhance Apoptotic Activity in A549 Lung Cancer Cells. Pharmaceuticals. 13(7).

Mourdikoudis S, Pallares R M, Thanh N T K. 2018. Characterization techniques for nanoparticles: comparison and complementarity upon studying nanoparticle properties 1110.1039/C8NR02278.11. Nanoscale. 10(27):12871-12934.

Patel N, Chotai N, Patel J, Soni T, Desai J, Patel R. 2008. Comparison of In Vitro Dissolution Profiles of Oxcarbazepine-HP b-CD Tablet Formulations with Marketed Oxcarbazepine Tablets. Dissolution Technologies. 15(4):28-34.

Qin L, He Y, Zhao X, Zhang T, Qin Y, Du A. 2020. Preparation, Characterization, and In Vitro Sustained Release Profile of Resveratrol-Loaded Silica Aerogel. Molecules. 25(12).

Salehi B, Mishra A P, Nigam M, Sener B, Kilic M, Sharifi-Rad M, Fokou P V T, Martins N, Sharifi-Rad J. 2018. Resveratrol: A Double-Edged Sword in Health Benefits. Biomedicines. 6(3).

Saralkar P, Dash A K. 2017. Alginate Nanoparticles Containing Curcumin and Resveratrol: Preparation, Characterization, and In Vitro Evaluation Against DU145 Prostate Cancer Cell Line. AAPS PharmSciTech. 18(7):2814-2823.

Sergides C, Chirila M, Silvestro L, Pitta D, Pittas A. 2016. Bioavailability and safety study of resveratrol 500 mg tablets in healthy male and female volunteers. Exp Ther Med. 11(1):164-170.

Springer M, Moco S. 2019. Resveratrol and Its Human Metabolites-Effects on Metabolic Health and Obesity. Nutrients. 11(1).

Tang C, Yin L, Yu J, Yin C, Pei Y. 2007. Swelling behavior and biocompatibility of Carbopol-containing superporous hydrogel composites. Journal of Applied Polymer Science. 104(5):2785-2791.

Wang P, Ren D, Chen Y, Jiang M, Wang R, Wang Y G. 2015. Effect of sodium alginate addition to resveratrol on acute gouty arthritis. Cell Physiol Biochem. 36(1):201-207.

Zhang L, Chen F, Zhang W, Wu Q. 2018. Kinetics and Characteristics of Soybean Oil and Protein Extracted by AOT Reverse Micelle Technology. Journal of Chemistry. 2018:1-11.

Zhang L, Zhang F, Fang Y, Wang S. 2019. Alginate-shelled SPI nanoparticle for encapsulation of resveratrol with enhanced colloidal and chemical stability. Food Hydrocolloids. 90:313-320.

Zheng H, Zhou Z, Chen Y, Huang J, Xiong F. 2007. pH-sensitive alginate/soy protein microspheres as drug transporter. Journal of Applied Polymer Science. 106(2):1034-1041.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of preparing an in situ gelling composition, comprising:
    wet granulating a mixture comprising a bioactive agent and soy protein in an aqueous granulation fluid to form granules, wherein the granulation fluid does not contain an organic solvent;
    mixing the granules with an aqueous solution containing sodium alginate to form a suspension, wherein the solution does not contain an organic solvent; and
    drying the suspension to form an in situ gelling film.

2. The method of claim 1, wherein the bioactive agent is resveratrol.

3. The method of claim 2, wherein the mixture contains a 5:5 to 5:7 ratio of resveratrol to soy protein.

4. The method of claim 1, further comprising incorporating the film into a solid dosage form.

5. The method of claim 1, further comprising reconstituting the film in water.

6. The method of claim 1, wherein the composition forms a gel phase when said composition comes into contact with an acidic media at a temperature at or above 35° C.

7. The method of claim 1, wherein the composition has a zeta-potential value of −0.235±0.012 mV.

8. The method of claim 1, wherein the film has an encapsulation efficiency of at least 96%.

9. The method of claim 1, wherein a ratio of sodium alginate to soy protein is 2:1.

* * * * *